United States Patent [19]

Thompson

[11] Patent Number: 5,662,654
[45] Date of Patent: Sep. 2, 1997

[54] BONE ANCHOR, INSERTION TOOL AND SURGICAL KIT EMPLOYING SAME

[75] Inventor: Ronald J. Thompson, Ft. Thomas, Ky.

[73] Assignee: Incont, Inc., Ft. Thomas, Ky.

[21] Appl. No.: 519,606

[22] Filed: Aug. 25, 1995

Related U.S. Application Data

[63] Continuation-in-part of Ser. No. 490,272, Jun. 4, 1995.
[51] Int. Cl.$^6$ .................................................. A61B 17/56
[52] U.S. Cl. .................. 606/72; 606/139; 606/144; 606/232; 128/DIG. 23; 128/DIG. 25
[58] Field of Search ................................ 606/72, 75, 113, 606/144, 139, 219, 220, 232; 600/30; 128/DIG. 23, DIG. 25

[56] References Cited

U.S. PATENT DOCUMENTS

| | | |
|---|---|---|
| 3,577,991 | 5/1971 | Wilkinson . |
| 3,877,434 | 4/1975 | Ferguson et al. . |
| 4,632,100 | 12/1986 | Somers et al. . |
| 4,669,473 | 6/1987 | Richards et al. . |
| 4,694,826 | 9/1987 | Chester . |
| 4,738,255 | 4/1988 | Goble et al. . |
| 4,898,156 | 2/1990 | Gattuma et al. . |
| 4,899,743 | 2/1990 | Nicholson et al. . |
| 4,938,760 | 7/1990 | Burton et al. . |

(List continued on next page.)

OTHER PUBLICATIONS

Anchor Fixation and Other Modifications of Endoscopic Bladder Neck Suspension. Theodore V. Benderev, MD, *Urology* (Nov. 1992) vol. 40, No. 5, pp. 409-418.

Bladder Neck Suspension for Needle Suspension Techniques, Mitek® Surgical Products, Inc. brochure (Aug. 1993).

Extraperititoneal Endoscopic Vesicourethral Suspension (EEVUS), Adley and Peter Albert; Current Surgical Techniques in Urology, Medical Publications, Inc. (1993), vol. 6, Issue 5, pp. 1-8.

Special Report: Laparoscopic Hysterectomy with Bilateral Salpingo-oophorectomy Using a Single Umbilical Puncture, Marco A. Pelosi, MD. et al., New Jersey Medicine, vol. 88, No. 10 (1988) pp. 721-726.

Laparoscopic Retropubic Colposuspension (Burch Procedure), C.Y. Liu, M.D. (Mar. 1993) pp. 1-12.

Laparoscopic Retropubic Cystourethropoxy Ceana H. Nezhat, M.D., et al., The Journal of the American Association of Gynecologic Laparoscopists (Aug. 1994) vol. 1, No. 4, Part 1, pp. 339-349.

The Marshall Marchetti-Krantz Surgical Technique for Urinary Stress Incontinence, Kermit E. Krantz, M.D., Litt. D., Mitek® Surgical Products, Inc. brochure (Aug. 1994).

(List continued on next page.)

*Primary Examiner*—Michael Buiz
*Assistant Examiner*—Mark S. Leonardo
*Attorney, Agent, or Firm*—Dinsmore & Shohl

[57] ABSTRACT

An anchor securable within a bore created in bone is provided. The anchor comprises: a body having a longitudinal axis, and proximal and distal ends; at least three wing members extending outwardly from, and secured to the body, each of the wing members capable of being elastically flexed from a normal deployed position to a compressed position, each of the wing members further having an external end positioned away from the body, at least a portion of the external ends of the wing members substantially aligned along a first imaginary plane extending through the body at an angle to a transverse cross-section through the body, this transverse cross-section perpendicular to the longitudinal axis of the body; and an aperture positioned adjacent the proximal end of the body. An anchor-insertion tool, a loaded anchor-insertion tool, and a surgical kit are also provided.

43 Claims, 17 Drawing Sheets

U.S. PATENT DOCUMENTS

| | | | |
|---|---|---|---|
| 4,946,468 | 8/1990 | Li . | |
| 4,968,315 | 11/1990 | Gatturna . | |
| 5,002,550 | 3/1991 | Li . | |
| 5,007,894 | 4/1991 | Enhorning . | |
| 5,013,292 | 5/1991 | Lemay . | |
| 5,013,316 | 5/1991 | Goble et al. . | |
| 5,019,032 | 5/1991 | Robertson . | |
| 5,037,422 | 8/1991 | Hayhurst et al. . | |
| 5,041,129 | 8/1991 | Hayhurst et al. . | |
| 5,046,513 | 9/1991 | Gatturna et al. . | |
| 5,078,730 | 1/1992 | Li et al. . | |
| 5,084,058 | 1/1992 | Li . | |
| 5,087,263 | 2/1992 | Li . | |
| 5,100,417 | 3/1992 | Cerier et al. . | |
| 5,133,723 | 7/1992 | Li et al. . | |
| 5,141,520 | 8/1992 | Goble et al. | 606/232 |
| 5,147,362 | 9/1992 | Goble . | |
| 5,163,946 | 11/1992 | Li . | |
| 5,174,087 | 12/1992 | Bruno . | |
| 5,176,682 | 1/1993 | Chow . | |
| 5,192,303 | 3/1993 | Gatturna et al. . | |
| 5,207,679 | 5/1993 | Li . | |
| 5,217,486 | 6/1993 | Rice et al. . | |
| 5,222,977 | 6/1993 | Esser . | |
| 5,224,946 | 7/1993 | Hayhurst et al. . | |
| 5,236,445 | 8/1993 | Hayhurst et al. . | |
| 5,250,055 | 10/1993 | Moore et al. . | |
| 5,258,016 | 11/1993 | DiPoto et al. . | |
| 5,268,001 | 12/1993 | Nicholson et al. . | |
| 5,269,809 | 12/1993 | Hayhurst et al. . | |
| 5,281,237 | 1/1994 | Gimpelson . | |
| 5,306,290 | 4/1994 | Martins et al. . | |
| 5,314,433 | 5/1994 | Li . | |
| 5,318,577 | 6/1994 | Li . | |
| 5,354,298 | 10/1994 | Lee et al. . | |
| 5,356,413 | 10/1994 | Martins et al. . | |
| 5,358,511 | 10/1994 | Gatturna et al. . | |
| 5,364,410 | 11/1994 | Failla et al. . | |
| 5,372,599 | 12/1994 | Martins . | |
| 5,376,096 | 12/1994 | Foster . | |
| 5,397,325 | 3/1995 | Della Badia . | |
| 5,411,506 | 5/1995 | Goble et al. | 606/104 |
| 5,411,523 | 5/1995 | Goble . | |
| 5,417,712 | 5/1995 | Whitaker et al. . | |
| 5,423,860 | 6/1995 | Lizardi et al. . | |
| 5,441,502 | 8/1995 | Bartlett . | |
| 5,486,197 | 1/1996 | Le et al. . | |
| 5,496,345 | 3/1996 | Kieturakis et al. . | |
| 5,505,735 | 4/1996 | Li | 606/72 |
| 5,505,736 | 4/1996 | Reimels et al. . | |
| 5,507,796 | 4/1996 | Hasson . | |
| 5,520,696 | 5/1996 | Wenstrom, Jr. . | |
| 5,520,700 | 5/1996 | Beyar et al. . | |
| 5,522,845 | 6/1996 | Wenstrom, Jr. . | |

OTHER PUBLICATIONS

A Modified Percutaneous Outpatient Bladder Neck Suspension System, Theodore V. Benderev, The Journal of Urology (Dec. 1994) vol. 152, pp. 2316–2320.

New Help for an Old Problem, Sue MacDonald, The Cincinnati Enquirer, Tempo Section E (Wednesday, Mar. 15, 1995) pp. E1 and E3.

Retropubic Bladder Neck Suspension System, Mitek® Surgical Products, Inc., brochure (Nov. 1994) Rev. B.

Spacemaker™ Surgical Balloon Dissector, General Surgical Innovations, Inc. brochure (1994).

Using the laparoscope for SUI, Robert L. Salerno, MD, Ph.D., Contemporary OB/GYN (Dec., 1994), pp. 35–40.

Mitek; Retropubic Bladder Neck Suspension System.

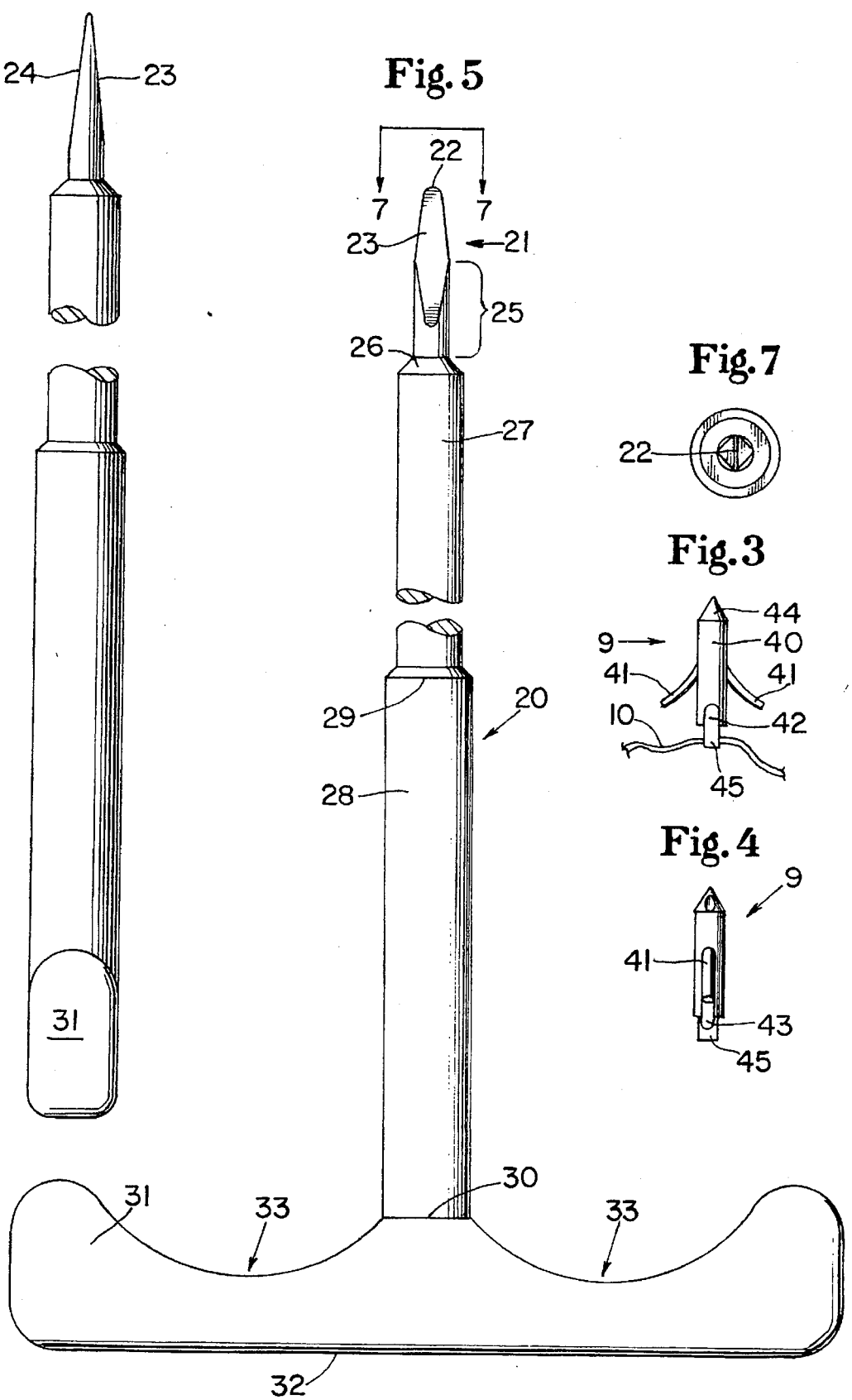

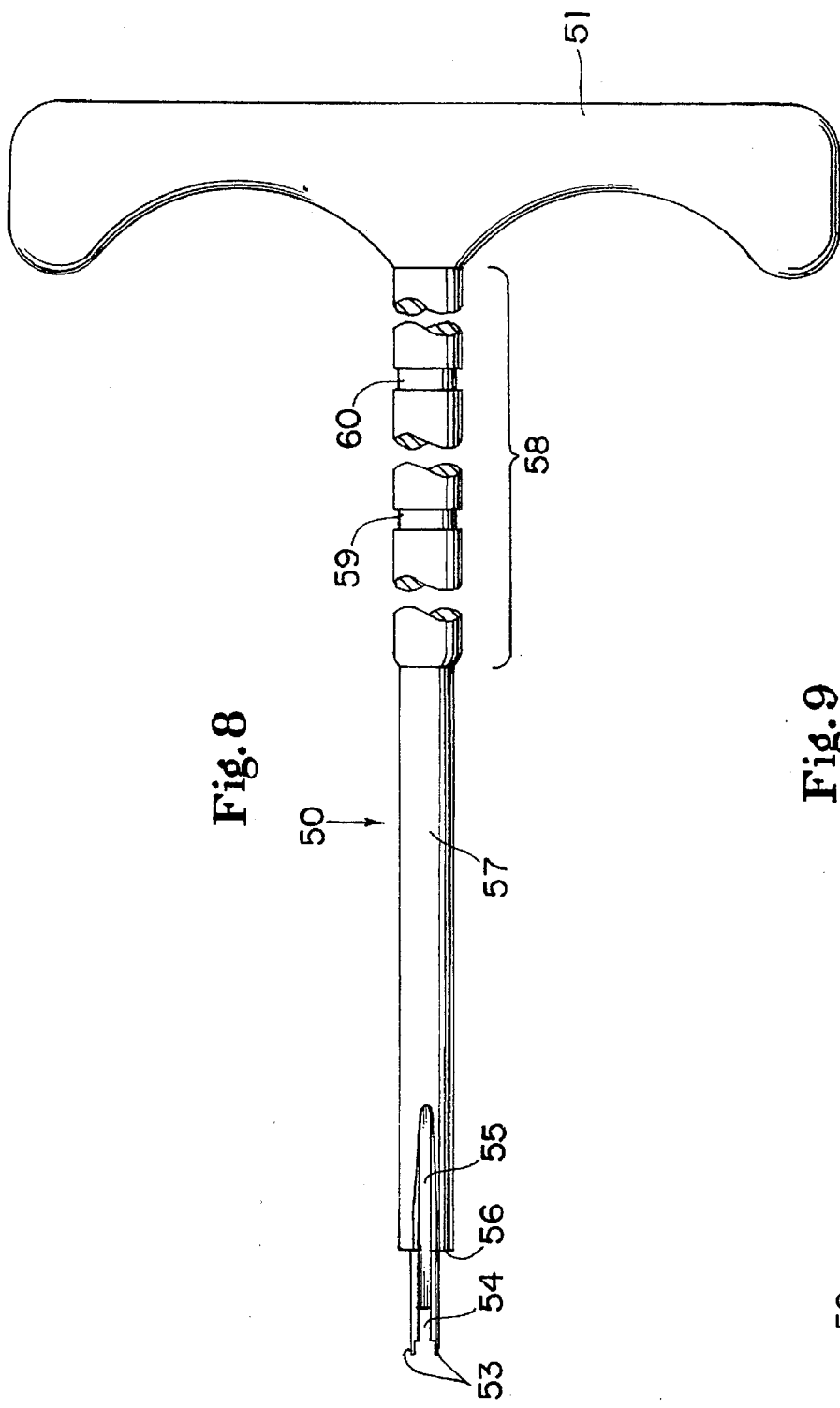
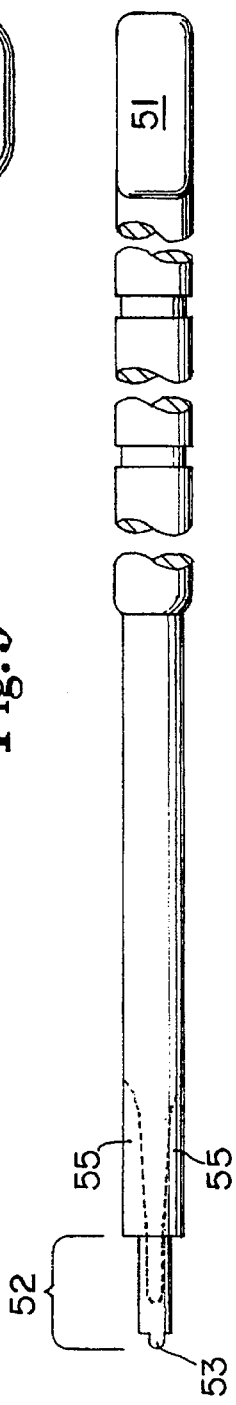

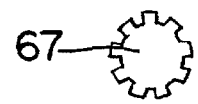
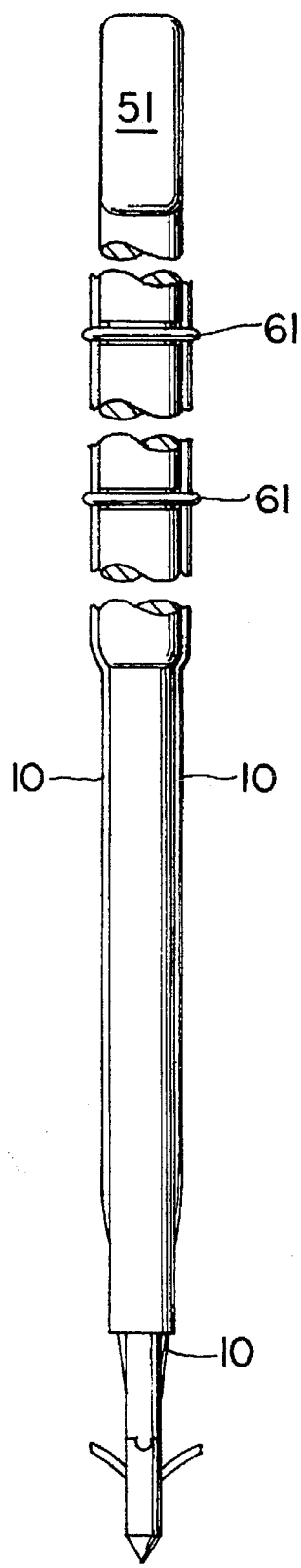
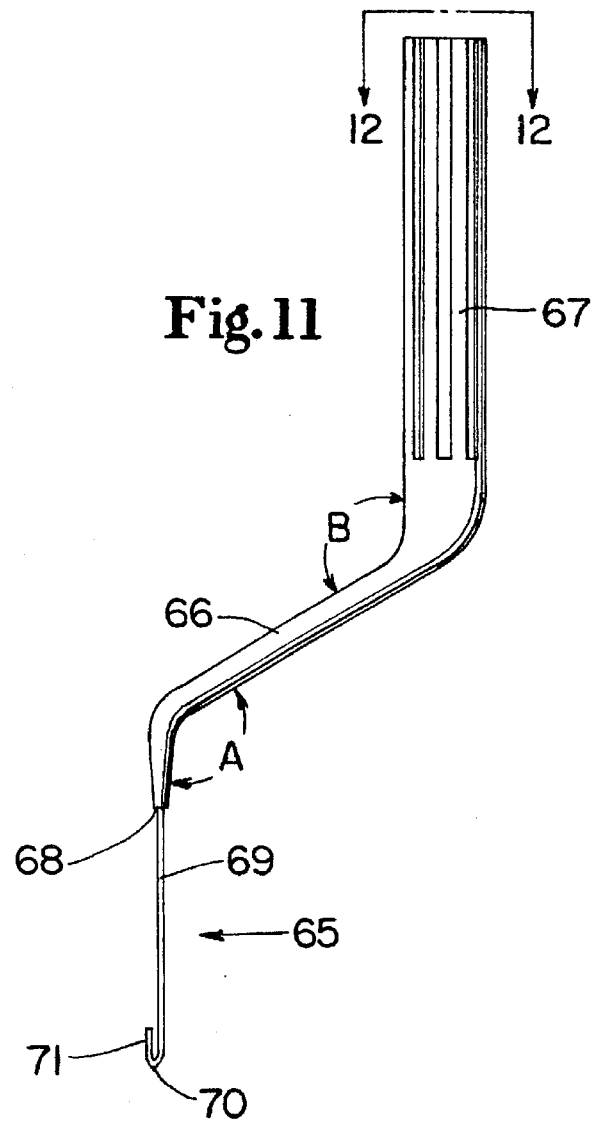

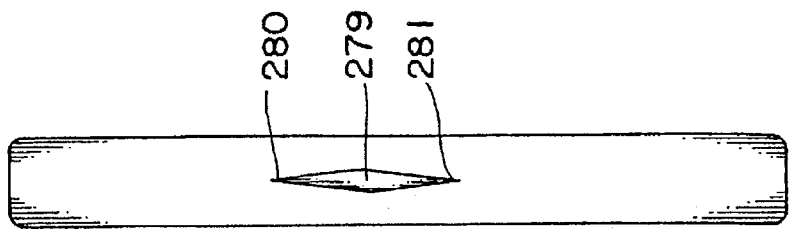
Fig.31a
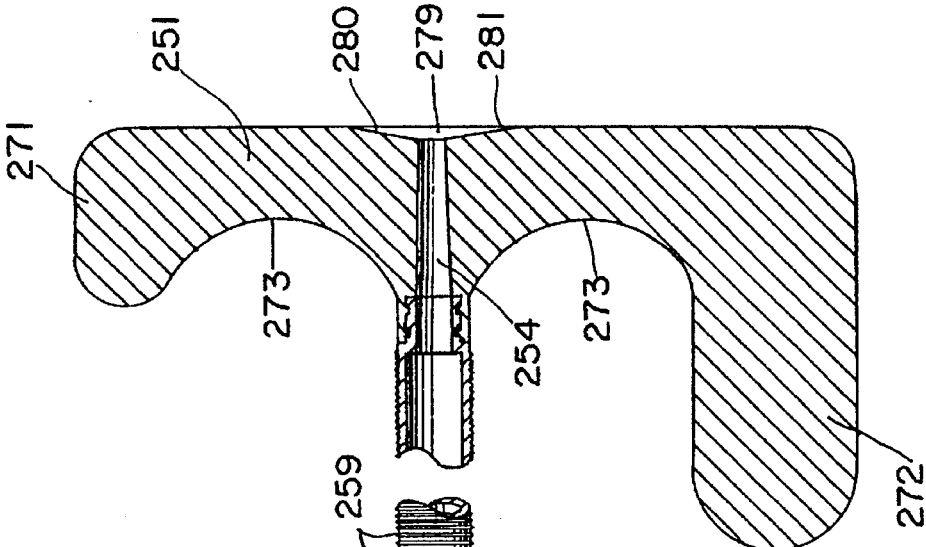
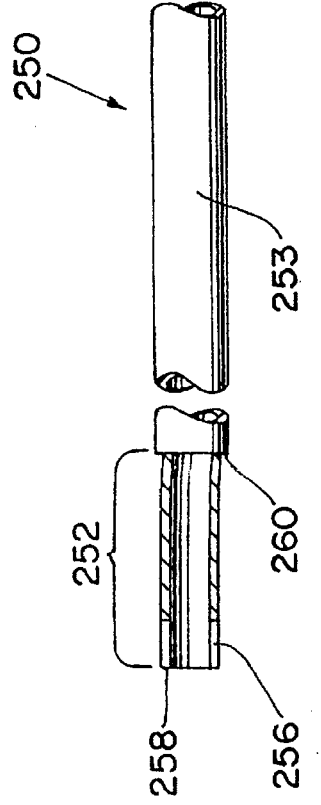
Fig.31

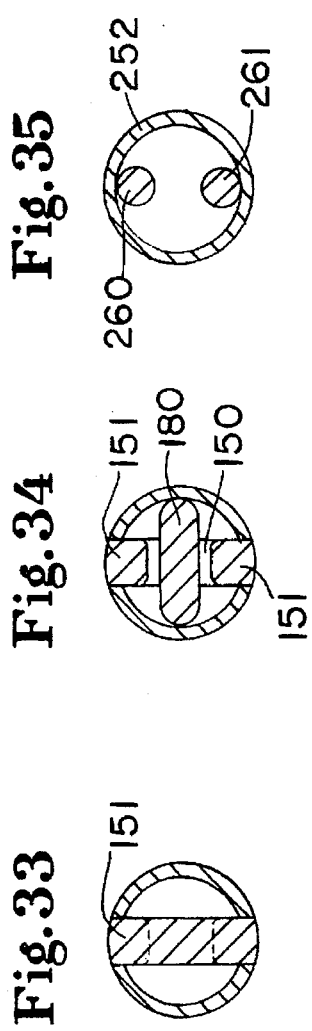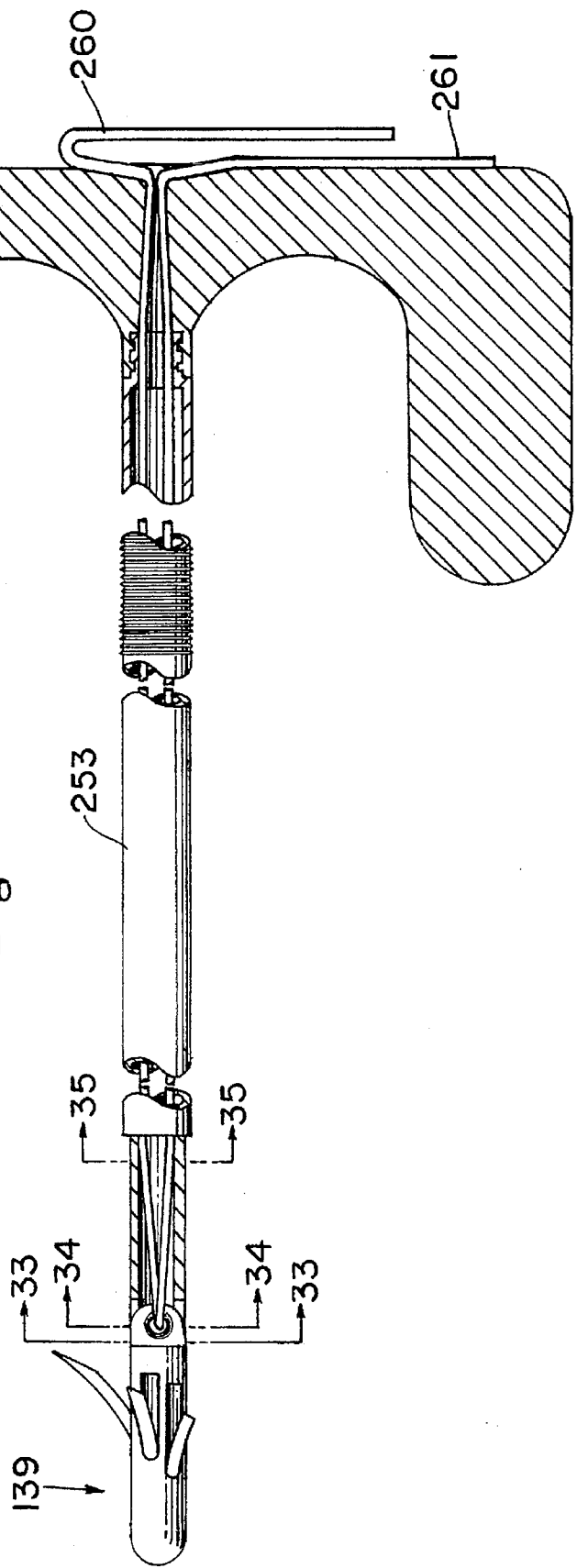

BONE ANCHOR, INSERTION TOOL AND SURGICAL KIT EMPLOYING SAME

This application is a continuation-in-part of pending application Ser. No. 08/490,272, filed Jun. 14, 1995.

BACKGROUND OF THE INVENTION

1. Field of the Invention

The present invention is directed towards a bone anchor, an anchor-insertion tool, and a surgical kit employing the same. These apparatus are particularly suited for a laparoscopic urethropexy procedure for the correction of female stress urinary incontinence. More particularly, the present invention provides apparatus for performing the urethropexy through laparoscopic techniques, thereby greatly reducing the duration, discomfort, and recovery period of such surgeries.

2. Description of Related Art

Female stress urinary incontinence (SUI), defined as the unintentional loss of urine, can be a socially unacceptable problem for many women. Most often, the incontinence occurs during coughing, sneezing, or physical activity in women afflicted with this problem. While effective surgical treatment for this condition has existed for nearly 50 years, the procedures typically involve major abdominal surgery with accompanying post-operative limitations lasting six to eight weeks. Because of the nature of these surgical procedures, many women simply resort to diaper-like incontinence pads, or simply avoid any activities which result in the unintentional loss of urine.

In the normal resting state, the external pressure exerted on the collapsible urethra by the surrounding musculature is greater than the pressure exerted on the bladder, and therefore continence is maintained. During moments of coughing, sneezing, or physical activities, greater pressure will be exerted on the dome of a filled bladder. In women not afflicted with stress incontinence, a corresponding increase in the external pressure on the urethra acts to prevent the unwanted loss of urine from the bladder. Sufferers of SUI, however, aren't so fortunate.

Stress incontinence is generally caused by two etiologies: a spastic detrusor muscle; or a loss of support of the periurethral tissue at the urethra-vesicular junction ("UVJ"—the region where the urethra enters the bladder). When the latter situation occurs, the UVJ will sag into the vagina, thereby reducing the pressure which can be exerted on the urethra during moments of stress. Diagnosis of any sagging of the UVJ can be easily determined by inserting the tip of a cotton swab into the urethra until it reaches the UVJ. The patient is then asked to bear down as if urinating, and loss of the UVJ support is readily identified by the upward movement of the wooden end of the cotton swab. In this test, the external urethral meatus acts as a fulcrum for the tip of the swab, and the elevation of the opposite end indicates the downward descent of the UVJ. U.S. Pat. No. 4,072,144 provides an alternative device which may be utilized to readily measure the angle of the UVJ in a similar manner.

The first urethropexy procedure for eliminating SUI caused by a sagging urethra was developed in 1948 by Drs. Marshall, Marchetti, and Krantz, and generally involves the fixation of the periurethral tissue at the UVJ on either side of the urethra (MMK procedure). Fixation in the MMK procedure, also known as urethropexy or abdominal culposuspension, is accomplished by suturing the periurethral fascia at the UVJ on either side of the urethra to the periosteum of the pubic bone. The procedure essentially alters the angular relationship between the urethra and bladder by elevating the UVJ, and therefore preventing the sagging of the UVJ when downward pressure is applied to the region by various stresses.

The MMK procedure has been perfected over the years, however the essential principles have remained the same. In 1955 Burch developed the technique of affixing the periurethral fascia bilaterally to Cooper's ligament, thereby resulting in a technically easier procedure because of the previous difficulties in passing a needle through the periosteum of the pubic bone. Although the Burch procedure has been performed laparoscopically, the five-year failure rate for the open Burch procedure is approximately 60%. A laparoscopic Burch procedure is even more problematic since it is extremely difficult and time-consuming to tie sutures laparoscopically.

Alternatively, urological procedures such as that of Stamey, Raz and Peyerra have been developed, however these are typically blind procedures which require the passing of long needles through the rectus fascia to the periurethral fascia utilizing a cystoscope. Although these urological procedures avoid the 10-centimeter midline or Pfannenstiel incision and its required three-day or longer hospital stay, the gynecological procedures of MMK, Burch and others have proven to be the most effective. In fact, the scarring of the urethra and interior bladder as well as the scarring of the periurethral tissues, aids in fixation of all of the involved tissues during the MMK and Burch procedures, thereby assisting in the prevention of incontinence.

Recently, a modified version of the MMK procedure has been developed which utilizes bone anchors secured directly to the pubic bone on either side of the symphysis for fixation of the UVJ. The apparatus for performing this modified MMK procedure are sold by Mitek Surgical Products, Inc. of Norwood, Mass., and a number of U.S. patents concern these products (see, e.g., U.S. Pat. Nos. 5,207,679, 5,217, 486 and 4,899,743). In the Mitek-MMK procedure, a Pfannenstiel incision must be made in the abdomen in order to provide access to the space of Retzius. The space of Retzius is in actuality a "potential" space in that it contains various connective tissues and fats which must be dissected in order to provide sufficient access to this region. In fact, this connective tissue, particularly the areolar adventitial tissue, generally breaks down after delivery of a child, and this breaking down of the connective tissue often contributes to the onset of SUI in many women.

Once the space of Retzius has been dissected in the Mitek-MMK procedure, small anchors are secured in the pubic bone on either side of the pubic symphysis. Each of the bone anchors has a suture attached thereto, and these sutures are threaded through the periurethral tissue on either side of the urethra. The sutures are then tied off in the abdomen so that the periurethral tissue is pulled upward, which in turn restores the angle of the urethra at the UVJ, thereby restoring the urethra to its proper location. While the Mitek-MMK procedure is highly effective, it is a lengthy and complicated procedure which can generally only be performed by highly-skilled surgeons.

The present invention offers an unique anchor design for use in a laparoscopic urethropexy procedure, as well as an inserter for placing the anchor within a bore created in the patient. These apparatus are particularly suited for laparoscopic urethropexy, however the use of the devices is not so limited.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

FIG. 3 is a top plan view of a bone anchor used in the method of the present invention;

FIG. 4 is a side plan view of the bone anchor of FIG. 3;

FIG. 5 is a top plan view of a drill tamper tool of the present invention wherein a portion of the tool has been broken-away;

FIG. 6 is a side plan view of the tamper tool of FIG. 5;

FIG. 7 is an end plan view of the tamper tool of FIG. 5, taken along line 7—7 thereof;

FIG. 8 is a top plan view of a bone anchor insertion tool of the present invention, wherein a portion of the tool has been broken-away;

FIG. 9 is a side plan view of the insertion tool of FIG. 8;

FIG. 10 is a side plan view of the insertion tool of FIG. 8 with the bone anchor of FIG. 3 loaded thereon;

FIG. 11 is a side plan view of a suture retriever of the present invention;

FIG. 12 is an end plan view of the suture retriever of FIG. 11, taken along the line 12—12 thereof;

FIG. 31 is a side plan view of an anchor-insertion tool of the present invention, wherein a portion of the tool has been cut-away for clarity;

FIG. 31a is an end plan view of the apparatus of FIG. 31;

FIG. 32 is a side plan view of the anchor-insertion tool of FIG. 31 with an anchor loaded thereon, said anchor having a suture extending therefrom, wherein a portion of the tool has been cut-away or cross-sectioned for clarity;

FIG. 33 is a cross-sectional view of the loaded anchor-insertion tool of FIG. 32 taken along line 33—33;

FIG. 34 is a cross-sectional view of the loaded anchor-insertion tool of FIG. 32 taken along line 34—34; and FIG. 35 is a cross-sectional view of the loaded anchor-insertion tool of FIG. 32 taken along line 35—35.

SUMMARY OF THE PREFERRED EMBODIMENTS

Figure 1:
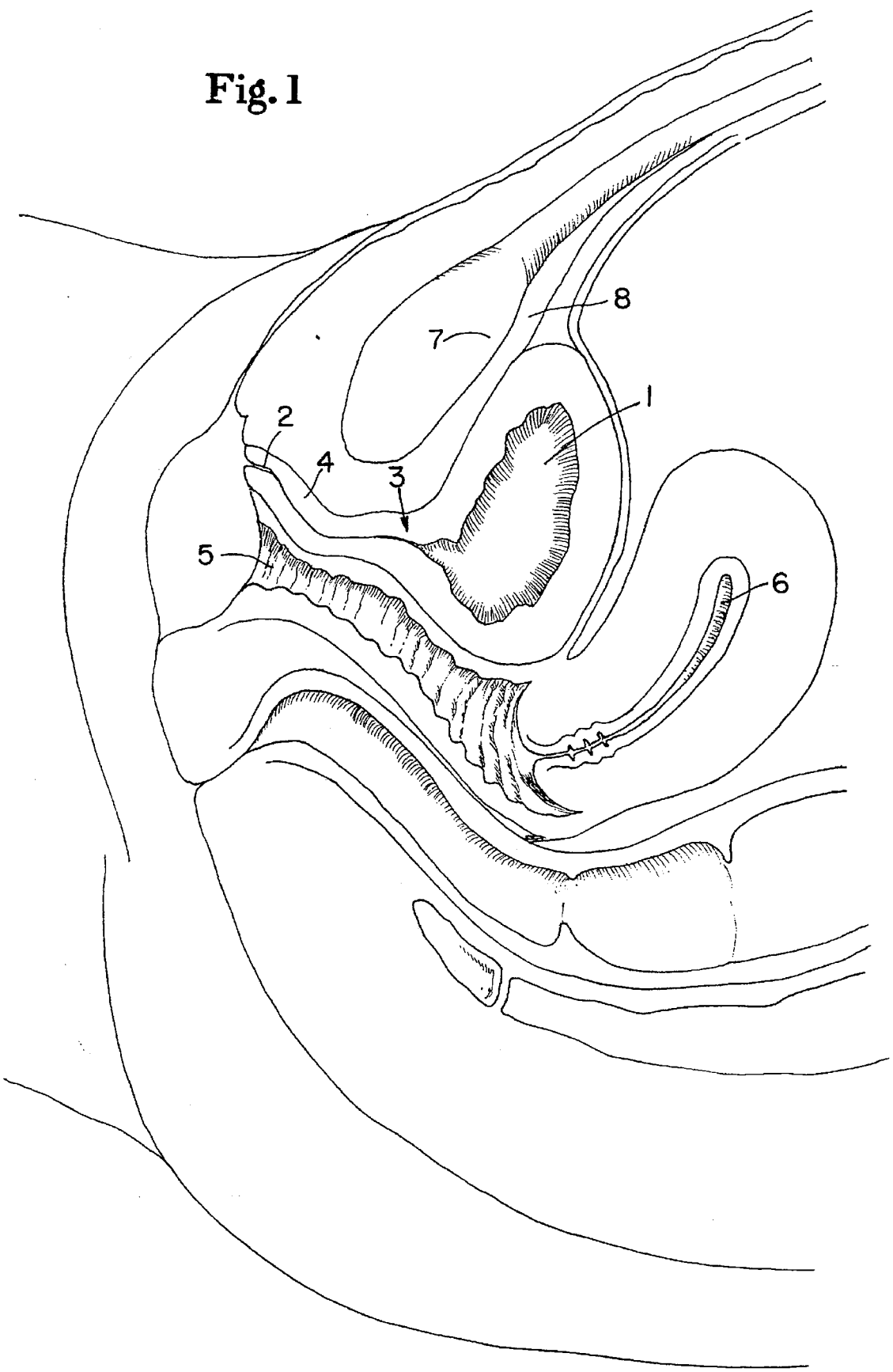
FIG. 1 is a cross-sectional view taken through the midline of a patient who has lost support of the periurethral tissue at the UVJ, and is thereby suffering from stress urinary incontinence.

In accordance with one aspect of the present invention, an anchor securable within a bore created in bone is provided. The anchor comprises:

(a) a body having a longitudinal axis, and proximal and distal ends;

(b) at least three wing members extending outwardly from, and secured to the body, each wing member capable of being elastically flexed from a normal deployed position to a compressed position, each wing member further having an external end positioned away from the anchor body, at least a portion of the external ends of the wing members substantially aligned along a first imaginary plane extending through the anchor body at an angle to a transverse cross-section through the body, this transverse cross-section perpendicular to said longitudinal axis; and (c) an aperture positioned adjacent the proximal end of the anchor body. The anchor body has upper and lower portions, and the top of the body is defined by a "top-line" extending along the surface of the body parallel to the longitudinal axis, such that the first imaginary plane described above intersects this top-line at the point of intersection between the surface of the body and the first imaginary plane which is nearest to the proximal end of the anchor body. The angle between the first imaginary plane and the transverse cross-section is between about 20° and about 60°, and most preferably about 45%

The anchor body should be cylindrical, and the proximal end of the anchor body is substantially perpendicular to its longitudinal axis to thereby provide a flat proximal end. A tab member extends from this flat proximal end, and the aperture described previously is preferably positioned in this tab member. The tab member preferably has a width less than the diameter of the anchor body to thereby provide a means for matingly engaging the proximal end of the anchor body with an anchor-insertion tool.

The wing members or barbs of the anchor may extend outwardly from the anchor body along a second imaginary plane extending through the body at an angle to a transverse cross-section through the body, wherein the transverse cross-section perpendicular to the longitudinal axis of the body. Alternatively, each of the wing members may extend outwardly from the body at points equidistant from the proximal end of the anchor body. In this case, the length of each of the wing members may then be chosen so that at least a portion of the external end of each wing member will be substantially aligned along the first imaginary plane.

The anchor body further comprises a channel positioned directly beneath each of the wing members, each channel having a length at least as great as the portion of its corresponding wing member positioned externally of the body, so that the wing members will be positioned at least partially within the channels when the wing members are in their compressed position. Each of the wing members preferably comprises a cylindrical barb which, in its deployed state, curvilinearly extends radially and axially away from said body. The external end of each barb is also preferably tapered so as to substantially align the entirety of each external end along said first imaginary plane. The channels are also preferably sized to accept the entirety of each barb upon compression.

The actual barb configuration may vary considerably, however embodiments having 3, 4 or 5 barbs are preferred. When 3 barbs are employed one of the barbs should extend downwardly away from the lower portion of the body, while the other two barbs extend upwardly from the upper portion of the body. More preferably, when viewed in a plan end view from the proximal end towards the distal end with the top-line of the anchor body defined as the 12 o'clock position, the 3 barbs are at the following positions: between about 10 and 11 o'clock; between about 1 and 2 o'clock; and about 6 o'clock. When four barbs are employed, two should extend downwardly away from the lower portion of the body, and two should extend upwardly away from the upper portion of the body. More preferably, the barbs are at the following positions: between about 10 and 11 o'clock; between about 1 and 2 o'clock; between about 4 and 5 o'clock; and between about 7 and 8 o'clock. When 5 barbs are employed, two should extend downwardly away from the lower portion of the body, and three should extend upwardly away from the upper portion of the body. More preferably, the barbs are at the following positions: about 12 o'clock; between about 10 and 11 o'clock; between about 1 and 2 o'clock; between about 4 and 5 o'clock; and between about 7 and 8 o'clock.

According to another aspect of the present invention, an anchor-insertion tool for laparoscopically inserting and securing the anchor described above is provided. This anchor-insertion tool comprises an elongate, rigid member having:

(a) an anchor-receiving tip capable of matingly engaging the anchor described above;
(b) a cylindrical, hollow intermediate portion having one end adjacent the, this intermediate portion having a diameter greater than the diameter of said anchor-receiving tip;
(c) a handle attached to the intermediate portion at the end opposite the anchor-receiving tip
(d) a passageway providing communication between the interior of the intermediate portion and the exterior of the tool, such that a suture extending from an anchor portioned on the anchor-receiving tip may pass from the anchor-receiving tip, through at least a portion of the intermediate portion, and through the passageway.

The anchor-insertion tool further comprises at least one, and preferably two notches for holding a suture, wherein the suture may be wedged within these notches in order to tension the suture between an anchor portioned on the anchor-receiving tip and the notches. Both of the notches are also preferably positioned adjacent the passageway so that suture tails exiting the passageway may be secured directly in the notches. Preferably the passageway extends through the handle, and has an elongated diamond-shaped exit such that the two notches comprise opposing corners of the diamond-shaped exit. In this manner, two tails of a single suture threaded through the aperture of an anchor held on the tip of the tool can be tensioned with the two tails separated from one another within the respective notches. This feature further helps in preventing the suture tails from becoming entangled with one another.

The anchor-receiving tip of the insertion tool is preferably hollow, with the interior of the tip in communication with the interior of the intermediate portion. The tip also preferably has a slot extending across the diameter of the tip and at least partially along the length of the tip, this slot positioned at an end of said tip opposite said intermediate portion. The tab member of the anchor should have a width equivalent to or less than the width of the slot so that the tab member may be positioned within the slot to thereby engage the anchor with the anchor-receiving tip. The anchor body and anchor-receiving tip should have approximately equivalent diameters, so that the end of the intermediate portion adjacent the tip may act as a stop when the loaded tool is employed to insert the anchor into a bore having a diameter less than the diameter of the intermediate portion. In addition, the interior diameter of the anchor-receiving tip is preferably greater than the sum of the width of the tab member plus twice the diameter of the suture, thereby permitting the tab member with the suture extending through the aperture to be positioned within the slot. To hold the anchor in place on the tip, a releasable adhesive may also be employed.

The handle may be threadably secured to the intermediate portion of the tool. The handle further preferably has a top portion and a bottom portion aligned with the slot in the anchor-insertion tip. The bottom portion may then be made heavier than the top portion in order to facilitate proper insertion of an anchor when the tool is employed. In addition, the intermediate portion of the tool has a plurality of ridges extending about its circumference positioned adjacent the handle. These ridges are sized so to interact with the operative channel of a laparoscope to provide enhanced control during use of the tool.

The present invention also provides a loaded anchor-insertion tool comprising, in combination, the anchor-insertion tool described above, the anchor described above, and a suture positioned within the aperture of the anchor. The anchor is matingly and releasably engaged with the anchor-receiving tip, and the suture extends from the anchor through the interior of the intermediate portion and through the passageway.

A surgical kit for performing laparoscopic urethropexy, is also provided. At a minimum, the kit may comprise a pair of loaded anchor-insertion insertion tools (i.e., each having an insertion tool, a loaded anchor, and a suture extending from the anchor). The kit may further comprise a drill tamper tool for laparoscopically creating a bore in the pubic bone of the patient, a suture retrieval tool, and one or more variously sized templates for guiding the suture through the periurethral fascia and vaginal mucosa adjacent the patient's urethra during the urethropexy procedure.

DETAILED DESCRIPTION OF THE INVENTION

Referring now to the drawings in detail, wherein like numerals indicate identical elements throughout the views, FIG. 1 is a cross-sectional view taken along the midline of a patient suffering from stress urinary incontinence. For reference, FIG. 1 depicts bladder 1, urethra 2, urethravesicular junction (UVJ) 3, periurethral tissue 4, vagina 5, uterus 6, pubic symphysis 7, and space of Retzius 8. In this patient, urethra 2 and the associated periurethral tissue 4 have sagged into vagina 5. During periods of stress such as coughing or sneezing, pressure will be exerted on bladder 1. Due to the collapse of urethra 2, the surrounding musculature will be unable to provide sufficient counteractive pressure on urethra 2 to prevent loss of urine during these periods of stress. As known from the methods of the prior art, particularly the MMK procedure, fixation of periurethral tissue 4 at UVJ 3 on either side of urethra 2 will act to support the urethra and prevent the sagging of urethra 2 into vagina 5. This in turn will enable the surrounding musculature to provide sufficient pressure on urethra 2 to prevent loss of urine during moments of stress.

Figure 2:
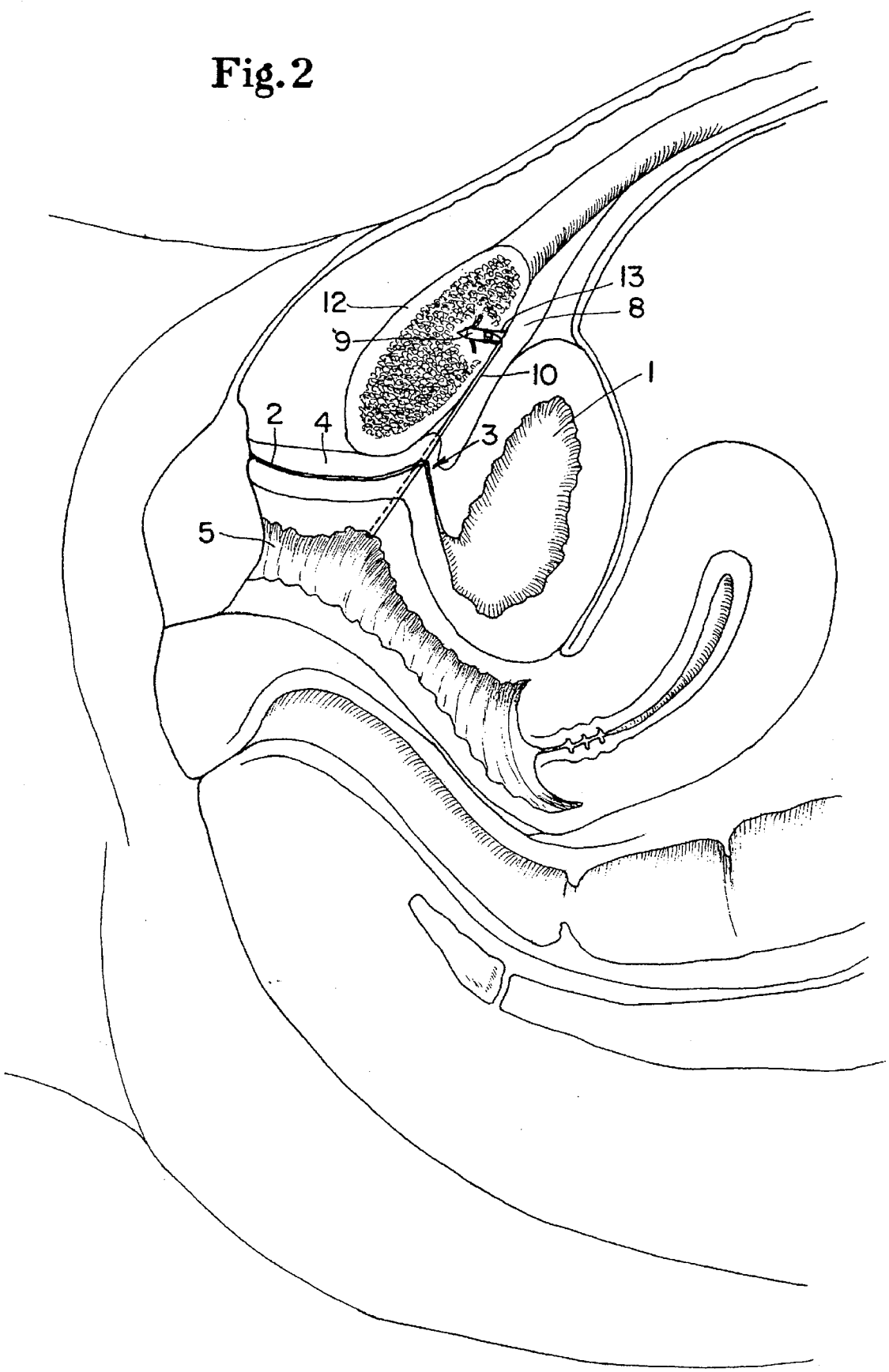
FIG. 2 is the same view as FIG. 1, however the structural defect has been corrected using the method and apparatus of the present invention.

FIG. 2 depicts the resulting support of urethra 2 at UVJ 3 by means of the surgical procedure of the present invention. It should first be noted that pubic bone 12 is shown in FIG. 2, and is that portion of the pubic bone lying immediately to the right of the pubic symphysis. As will be more fully understood later, the anchors of the present invention are secured in the pubic bone on either side of the pubic symphysis. A bore 13 has been produced in pubic bone 12, and anchor 9 has been secured within bore 13. It should be noted that bore 13 and anchor 9 have been enlarged for purposes of clarity. A suture 10 is secured to anchor 9, and the two tails of suture 10 extend downwardly through the space of Retzius 8 into vagina 5. The tails of suture 10 extend into the vagina immediately to the right of urethra 2 through periurethral tissue 4 at UVJ 3. In the vagina, the two tails of suture 10 are tied to one another such that suture 10 provides an upward force on periurethral tissue 4 on the right side of urethra 2 adjacent UVJ 3. An identical anchor and suture combination is secured to the pubic bone on the left side of the pubic symphysis, and the suture enters the vagina in a similar fashion as before in order to provide an upper force on periurethral tissue 4 on the left side of urethra 2. In this fashion, the sutures on either side of the urethra act to restore the angle of the urethra at the UVJ.

As will be described in further detail below, the securing of the anchors to pubic bone 12 can be accomplished laparoscopically. Suture 10 may then be pulled into vagina 5 through periurethral tissue 4 immediately adjacent to urethra 2. The two tails of suture 10 may then be tied to one another within vagina 5 by hand. It has been found that the portion of suture 10 positioned within vagina 5 will be epithelialized within a few days after the procedure. In this fashion, suture 10 will not cause any discomfort or irritation to the patient since suture 10 will quickly be covered by the epithelium of vagina 5.

SURGICAL TECHNIQUE

A. Preparatory Procedures

Identification of patients suitable for the techniques of the present invention may be made by any of the known techniques for identifying patients amenable to SUI correction by MMK or similar procedures. For example, as discussed previously a cotton swab may be inserted into the urethra until the end of the swab reaches the UVJ. The patient is then asked to bear down and the movement of the portion of the swab outside of the urethra is monitored. The external urethral meatus will act as a fulcrum for the cotton swab, and a loss of urethral support at the UVJ can be readily identified by the upward movement of the external end of the cotton swab. This indicates a downward descent of the urethra at the UVJ, which in turn provides an indication of the structural cause of the patient's SUI. Other means known in the art, however may be employed to confirm the diagnosis and/or to rule out other possible causes.

The preoperative preparation of the patient follows standard procedures for laparoscopic and gynecological surgeries, however no enema is needed. The patient is placed in the dorsal lithotomy position, and standard parenteral antibiotics are applied. Preferably, the patient is also placed under general anesthesia in order to minimize discomfort.

Figure 17:
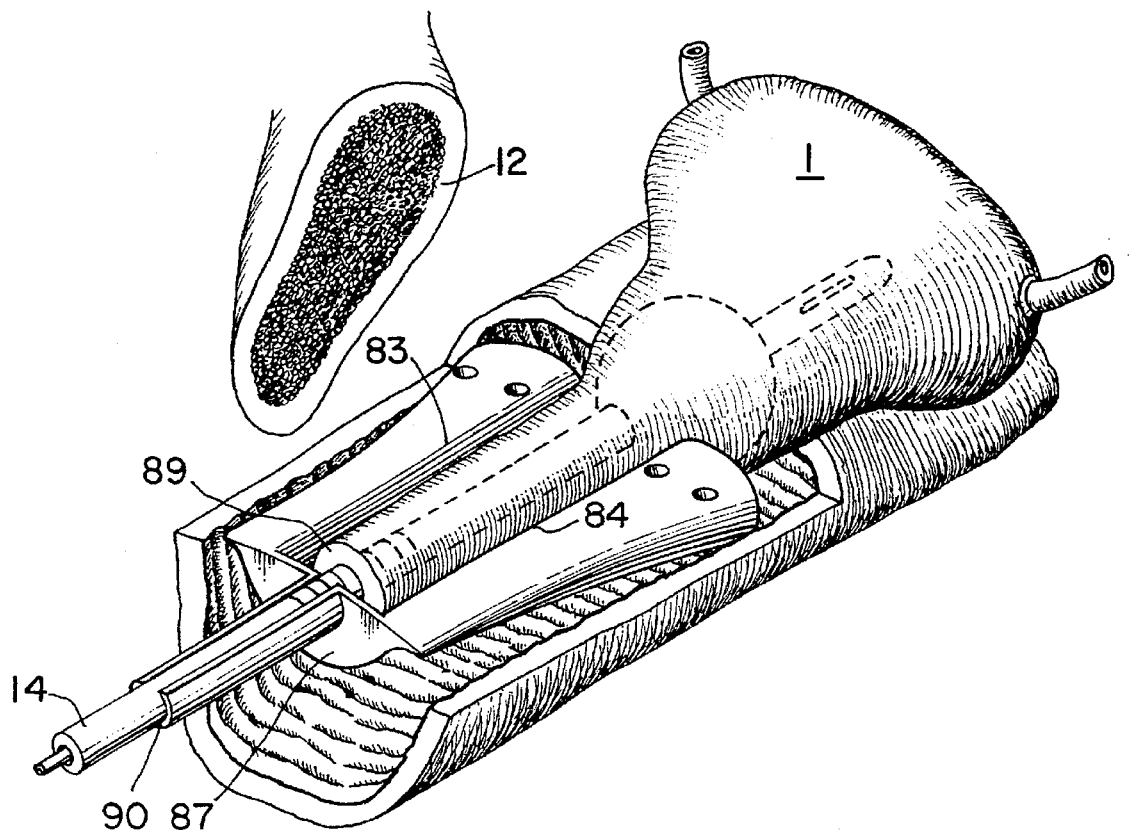
FIG. 17 is a perspective view of the template of FIG. 13 in use during a surgical procedure with portions of the patient's anatomy cut-away for clarity.

A Foley catheter (16 French with 10 cc balloon) is then inserted into the urethra. The balloon of the Foley catheter is inflated, and the catheter is gently pulled outwardly to ensure proper placement of the balloon at the juncture of the bladder and the urethra. Proper placement of Foley catheter 14 is shown in FIG. 17 wherein a portion of vagina 5 has been cut-away for purposes of clarity. Bladder 1 is thereafter drained in the usual fashion using the Foley so that the bladder will become deflated. As will be understood below, maintaining the bladder in a deflated state greatly simplifies the procedure of the present invention. In addition, when the template of the present invention is employed, it is preferable that Foley catheter 14 be positioned in the manner shown in FIG. 17 for reasons which will be described further herein.

It is also desirable to measure the length of the patient's urethra in order to ensure proper placement of the supporting sutures, particularly when the template of the present invention is employed. If the sutures are placed too close to the bladder, there is a considerable risk that the suture retrieving tool will puncture the bladder. Likewise, if the sutures are placed too far from the UVJ, then proper support of the urethra will not be accomplished. The length of urethra 2 may be readily measured by means of any suitable apparatus which may be inserted into the urethra, as long as the surgeon can be certain that one end of the device is positioned at the juncture of the bladder and the urethra (i.e., the UVJ). The simplest means of obtaining this measurement is to provide graduations along at least a portion of the length of Foley catheter 14, as shown in FIG. 17. In this fashion, when the balloon of the Foley is properly inflated within the bladder and the catheter pulled outwardly to ensure proper seating of the balloon at the juncture of the bladder and the urethra, the length of the urethra can be determined using the graduations which will be readily visible immediately adjacent the end of urethra 2. While the average urethra is 3 cm in length, this can often vary between about 2.7 and about 3.3 cm. As will be more fully understood below, the suture template employed in the method of the present invention can thus be manufactured in different sizes to accommodate the differing urethra lengths. A minimum of two sizes for the template may be provided, and more preferably at least three different sizes. Alternatively, the graduations may be employed to facilitate proper placement of a single-sized template.

After the placement of Foley catheter 14 and drainage of bladder 1, an infraumbilical incision is made in the patient in order to provide access to the pre-peritoneat region (the area between the abdominal wall and the peritoneum), and more particularly space of Retzius 8. Surgical dissection of space of Retzius 8 is necessary in order to provide visual access to the pubic bone for placement of the bone anchors. Thus, dissection is performed below the fascia, thereby eliminating the adventitial or supportive connective tissue in space of Retzius 8. Although dissection of the connective tissue in space of Retzius 8 can be accomplished in the typical fashion through a laparoscope, Applicant has found that a balloon dissection procedure is simpler and more effective.

Balloon dissection can be accomplished using the SPACEMAKER surgical balloon dissector manufactured by General Surgical Innovations of Portola Valley, Calif., or an equivalent device. This device has a guide rod to which a small balloon is attached. The guide rod is inserted into the infraumbilical incision until the tip of the rod reaches the pubic symphysis in the space of Retzius (i.e., between the symphysis and the bladder). The balloon is then inflated in space of Retzius 8 by filling the balloon with approximately 300 cc of saline solution or other suitable fluid, thereby further deflating bladder 1 and separating the surrounding connective tissue in order to provide sufficient room in space of Retzius 8 for the fixation procedure of the present invention. The balloon is then aspirated and removed from the pre-peritoneal region.

Although the SPACEMAKER device has an integral trocar which may normally be left in the infraumbilical incision for placement of the laparoscope; the only size currently available is too small for the procedure of the present invention. Obviously a properly sized integral trocar could remain in the patient after removal of the deflated balloon. Alternatively, and as presently preferred, the SPACEMAKER device is removed in its entirety, and a larger 12 mm trocar is inserted into the infraumbilical incision. A 12 mm WOLF operating/laser laparoscope (preferably with a WOLF 50/50 beamsplitter camera) is inserted into the trocar. The pre-peritoneal region is then insufflated, preferably with $CO_2$ at a pressure between about 10 and about 30 mm Hg, thereby further expanding the space of Retzius and providing excellent laparoscopic vision in this region.

Although the balloon dissection procedure is highly effective, further dissection of the space of Retzius is typically necessary in order to provide the necessary access to the pubic bone and the periurethral tissue. Although this may be accomplished by means of a $CO_2$ laser or a electrocautery device through the laparoscope already inserted, it is presently preferred that an additional 5 mm trocar be inserted in the midline suprapubically. A irrigation/suction/boyle device (such as that manufactured by US Surgical) is then inserted into the space of Retzius through the smaller trocar. This device will not only assist in further dissection of the space of Retzius, but will also provide the necessary irrigation and suction while the other instruments necessary for performing the present procedure are employed through the infraumbilical trocar. The result of further dissection is that vision far superior to the standard MMK or Burch procedures employing a full abdominal incision will be provided, since it is difficult in these procedures for the surgeon to see the underside of the pubic bone where the anchors must be placed without the surgeon placing his or her head on the stomach of the patient. In this fashion, unobstructed laparoscopic access to the pubic bone and the periurethral tissue necessary for performing the procedure of the present invention is provided.

B. Creation of Bore in Pubic Bone

It should initially be noted that the procedure of the present invention may be employed with any of a variety of bone anchors, provided that the anchor can be readily secured to the pubic bone and a suture can be attached thereto. It is presently preferred, however, that the MITEK bone anchors known to those skilled in the art be employed for this purpose. As discussed more fully herein, these anchors are secured in place by pressing them into properly-sized bores created in the pubic bone.

The MITEK-MMK and related procedures require the use of either a mechanical drill or hand-operated awl in order to provide the bore for insertion of a bone anchor (such as those manufactured by Mitek Surgical Products, Inc.) into the pubic bone. While these devices may be readily employed with large abdominal incisions, they cannot be used through a laparoscope for a number of reasons. Most importantly, these tools must be sufficiently sharp to enable the surgeon to penetrate the hard outer layers of the pubic bone (periosteum and cortical bone). Since the field of vision through a laparoscope may be limited at times, however, it is very risky to employ such sharp implements as there is a tremendous risk of puncturing the bladder or other soft tissue in the operative area. In addition, as best shown in FIG. 12, pubic bone 12 falls away from the laparoscope at an angle of approximately 45°. The angularity of pubic bone 12 therefore provides vision and operative difficulties which are overcome by the apparatus and methods of the present invention. Simply drilling into pubic bone 12 using prior art apparatus through the laparoscope is not advisable because the drill or awl tip will tend to slide downwardly during the drilling operation because of the manner in which pubic bone 12 angles downwardly away from the laparoscope. While the drill tip may eventually penetrate the hard outer periosteum of the bone, the drill may enter at an improper location or angle due to downward slippage of the drill tip. Ideally one would like to produce a bore in pubic bone 12 which is at an angle of approximately 45-degrees to the surface of the bone into which the bore is produced. This angle may, however, be between about 20 and about 60-degrees, to thereby provide sufficient support for the bone anchor to be placed in the bore thus produced.

Applicant has developed a novel method and apparatus for creating the required bores in the pubic bone through a laparoscope. The method and apparatus avoid the use of any sharp tips, while still enabling the surgeon to properly place the bores in the pubic bone without a risk of misalignment during the bore creation process. In order to produce the bore without a need for a sharp instrument, a laser is first employed to produce a cone-shaped crater in the pubic bone at the desired bore location. The crater is produced in the periosteum and cortical bone, thereby providing access to the soft cancellous, or tribecular, bone. In this fashion, a drill tamper tool (to be described further herein) may then be employed to create the properly-sized bore.

Figure 21:
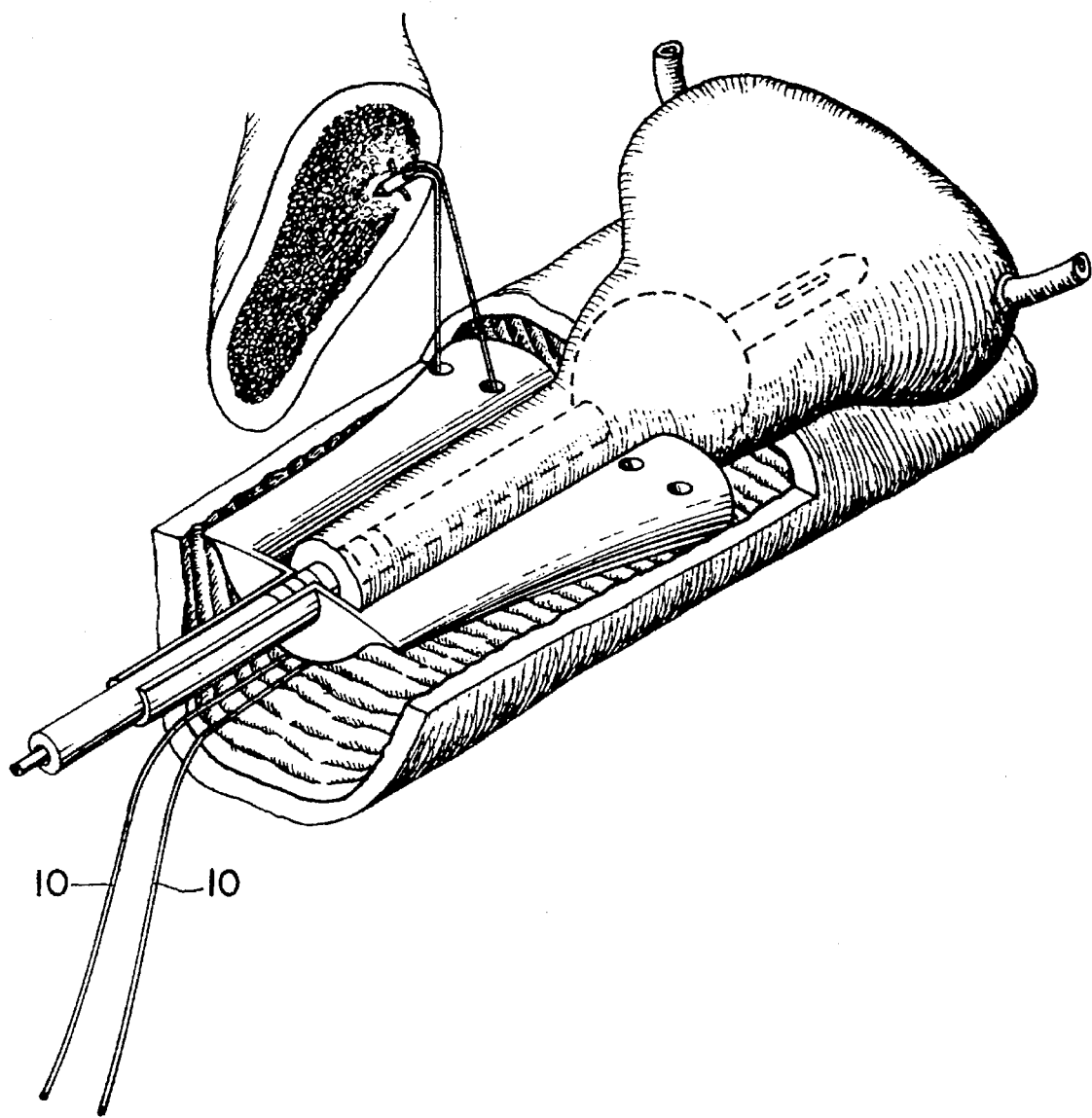
FIG. 21 is a perspective view of the surgical procedure of the present invention wherein portions of the patient's anatomy cut-away for clarity, and wherein the sutures have been retrieved from the pre-peritoneal region for tying.
Figure 22:
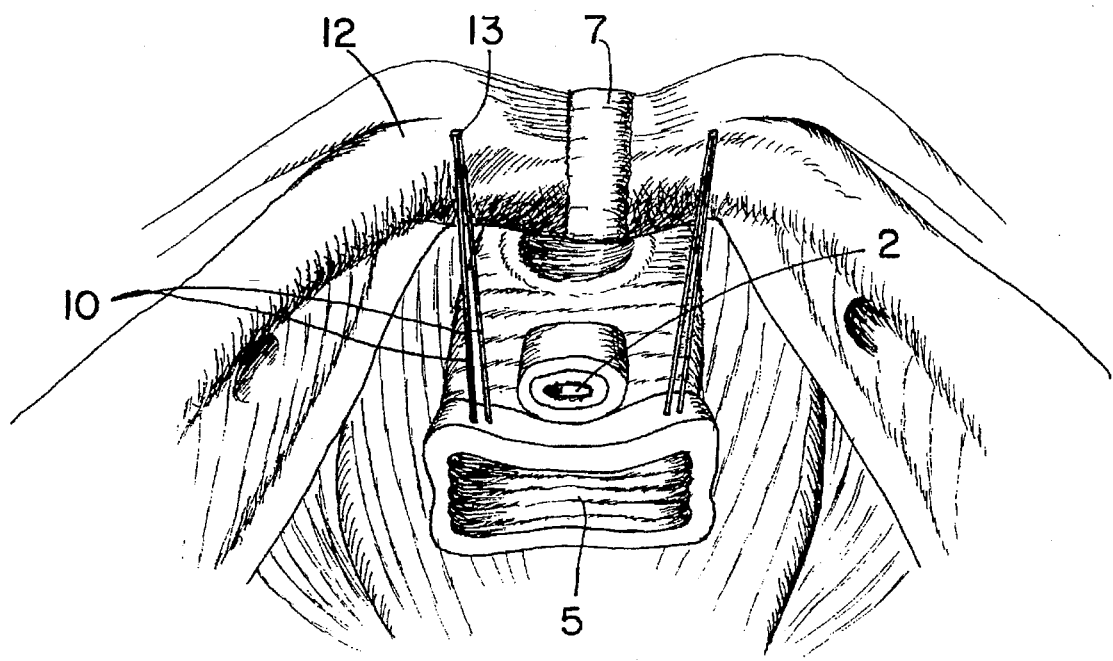
FIG. 22 is a perspective view of the space of Retzius, and illustrates the proper placement of the anchors and sutures employed in the present invention.

In order to create the starter "crater" in the pubic bone, a $CO_2$ laser (such as a SHARPLAN 20 watt) is inserted through the laparoscopic channel, and is employed to create a cone-shaped crater slightly larger than the diameter of the laser beam in the pubic bone on either side of the pubic symphysis. The diameter of the laser beam is preferably about 2 mm, and therefore the cone-shaped crater created in the pubic bone is slightly larger than 2 mm in diameter. The crater should be sufficiently deep to reach the cancellous bone. A crater is established on either side of the pubic symphysis directly above and approximately 1 cm lateral to the periurethral fascia at the UVJ. FIG. 21 depicts the space of Retzius after creation of bores 9 and 17 in pubic bone 12 on either side of pubic symphysis 7. The desired placement location can be readily determined through means of the optics of the laparoscope, as proper dissection of space of Retzius 8 will provide sufficient vision for proper identification of the appropriate structures in the patient. If needed, the surgeon may use one or more fingers to press upwardly on the periurethral tissue on either side of the urethra within the vagina in order to properly position the two starter craters in the pubic bone.

Once access to the cancellous bone has been provided by the cone-shaped craters created on either side of the pubic symphysis using the laser, the bore for insertion of the anchor may be readily created using the drill tamper tool of the present invention. Since the cancellous bone is significantly softer than the periosteum or cortical bone, it is not necessary that a sharp awl or drill bit be used to create the bore. Rather, a bluntly pointed drill tamper tool may be used, wherein the end of the tamper tool is not sufficiently sharp to puncture the bladder or other soft tissue under normal use. This provides a significant advantage in that damage to the bladder or other soft tissue structures and the patient may be readily avoided, and drill guides and the like which must be used with the MITEK Instruments and similar apparatus can be avoided. As will be understood, the MITEK drill guides cannot possibly be employed laparoscopically. The laser employed to create the cone-shaped craters can be readily aligned in the proper location, without risk of slippage or other inadvertent movement during the procedure. The laser-created craters can then be readily employed to insure that the bores for anchor placement are created in the exact, desired location.

The drill tamper tool of the present invention is shown in FIGS. 5–7, and comprises an elongate rigid member 20 having a distal end which comprises a conical boring tip 21. End 22 of conical boring tip 21 preferably has a cross section similar in size and shape to the crater created in the pubic bone by the laser. In this fashion, alignment of conical boring tip 21 within the crater will be relatively easy. It is also preferred that end 22 of conical boring tip 21 be blunt so that it will not penetrate soft tissue such as the bladder during normal use (i.e., not sufficiently sharp to penetrate soft tissue or organs during normal use). Certainly, however, conical boring tip 21 should be sufficiently thin and blade-like to permit boring tip 21 to create the bore in the soft cancellous bone by use of hand force through the laparoscope. In this regard, conical boring tip 21 is preferably shaped similar to a flat bladed screwdriver. Thus, boring tip 21 has tapered side surfaces 23 and 24 which terminate in portion 25 which is of a circular cross-section. The diameter of circular-crossection portion 25 is identical to the diameter of the bore which will be created in the pubic bone. By rotating the drill tamper tool while simultaneously pressing boring tip 21 into the crater in the pubic bone, the desired bore will be readily created therein. The diameter of portion 25 is also approximately the same as the body of the anchor to be inserted into the bore.

In order to ensure sufficient support for the bone anchors of the present invention, it is also important that the anchor be seated deep within the pubic bone. In order to ensure proper depth of the bore, therefore, collar 26 is provided on the drill tamper tool. Collar 26 is of a larger diameter than conical boring tip 21, and therefore will act as a stop preventing further penetration of the drill tamper tool into the bone. Although collar 26 is shown as tapering in diameter between conical boring tip 21 and intermediate portion 27, it is also possible that collar 26 simply comprise a non-tapered end of intermediate portion 27. Intermediate portion 27 has a diameter significantly greater than that of conical boring tip 21, and is positioned on the opposite end of collar 26. Intermediate portion 27 not only allows the provision of collar 26, but also adds rigidity to the tamper tool. Intermediate portion 27, however, should be significantly smaller in diameter than the operative channel of the laparoscope so that sufficient vision of the operative region is provided. Preferably, the length of conical boring tip 21 is between about 1, and 3 cm, and most preferably about 1.4 cm. Intermediate portion 27 is preferably between about 2, and 6 cm, and most preferably about 5 cm.

In order to provide stability during the boring procedure, cylindrical guide portion 28 is also included on the drill tamper tool. Guide portion 28 has first end 29 and second end 30. First end 29 is attached to intermediate portion 27 at the opposite end of collar 26. Cylindrical guide portion 28 preferably has a diameter slightly less than the operative channel of the laparoscope. In this fashion, guide portion 28 provides the necessary stability within the laparoscope to ensure proper placement of the bores. Second end 30 of guide portion 28 is preferably attached to handle 31. While handle 31 is shown as having a flat end portion 32 and curved hand grip surfaces 33, handle 31 can be of a variety of forms and still be sufficient for purposes of the present invention. Handle 31 facilitates the proper manipulation of conical boring tip 21 through the laparoscope, and provides a sufficiently firm surface 32 upon which force may be applied to complete the boring operation. Guide portion 28 preferably has a length between about 50 and about 55 cm, and most preferably about 52 cm. The overall length of the drill tamper tool of the present invention therefor permits sufficient access to the pubic bone, while also providing an ergonomically-effective boring operation through the laparoscope and ensuring that the tool does not interfere with the anesthesiologist.

C. Insertion of Bone Anchors in Pubic Bone

The preferred anchor for use in the present invention is shown in FIGS. 3 and 4, and is identical to that disclosed in U.S. Pat. No. 5,207,679, which is herein incorporated by reference. Anchor 9, which is preferably made of titanium alloy or other suitable material, has a cylindrical body 40 and a conical end 44 attached thereto. At least two flexible barbs 41 curve outwardly away from body 40. A groove 42 is provided on either side of body 40 at the end opposite to conical end 44. In addition, cylindrical end 45 extends away from body 40 adjacent groove 42. The longitudinal axis of cylindrical end 45 is aligned with the longitudinal axis of body 40. The diameter of cylindrical end 45 is preferably equivalent to the diameter of body 40 within grooves 42 positioned on opposite sides of body 40. As will be understood below, this structure facilitates the attachment of anchor 9 to an insertion tool.

As best shown in FIG. 4, body 40 and cylindrical end 45 have an aperture 43 provided therethrough. Aperture 43 is sized so as to accommodate a suture appropriate for the fixation procedure of the present invention. It is preferred that a size 0 GORE-TEX suture be employed, and thus anchor 9 and its accompanying aperture 43 should be sized accordingly. The use of a GORE-TEX suture is preferred for reasons of strength and non-elasticity. Certainly other types of sutures could be employed if necessary. A portion of suture 10 is shown in FIG. 3 having been inserted through aperture 43.

The insertion of anchor 9 is relatively straightforward, and merely requires that the anchor be pressed completely into the bore which has previously been created in the pubic bone. Preferably, anchor 9 is inserted into the bore in the pubic bone until conical end 44 reaches the distal end of the bore. The bore should be at least as long as the length of anchor 9, however, it is preferably considerably longer to ensure sufficient support for the anchor. As anchor 9 is pressed into the bore, flexible barbs 41 will be compressed against body 40 as they are inserted past the hard periosteum and cortical bone surrounding the bore. Once within the bore, however, flexible barbs 41 will tend to spring back into the soft cancellous bone, thereby securing the anchor in place. A slight tug on the tails of the suture 10 will also cause barbs 41 to further deploy.

In order to insert anchor 9 into the bore previously created in the pubic bone, the anchor insertion tool shown in FIGS. 8–10 may be employed. Thus, after the drill tamper tool has been employed to create the necessary bores, the anchor insertion tool of the present invention having an anchor and threaded suture loaded thereupon, is inserted into the laparoscope for proper seating of anchor 9.

The anchor insertion tool of the present invention comprises a rigid elongate member 50 having a handle 51 at one end, and an anchor-receiving tip 52 at the opposite end of elongate member 50. As was the case with the drill tamper tool, handle 51 can be of any variety, and that shown is only the presently-preferred embodiment of this handle. Anchor-receiving tip 52 is similar in construction to that shown in FIGS. 4–6 of U.S. Pat. No. 5,207,679. Anchor-receiving tip 52 is constructed so as to matingly receive anchor 9 in order to facilitate insertion of anchor 9 into the bore. As will be apparent, the longitudinal axis of anchor-receiving tip 52 should be aligned with the longitudinal axis of elongate member 50. Anchor-receiving tip 52 is cylindrical in nature, having a diameter approximately equivalent to body 40 of anchor 9. In this manner, at least a portion of anchor-receiving tip 52 may pass through the bore in the pubic bone during the anchor insertion process to properly seat the anchor completely within the bore.

Anchor-receiving tip 52 has a pair of guide tabs 53 extending from the end of anchor-receiving tip 52 on either side thereof. Guide tabs 53 are sized and shaped so as to be matingly received within grooves 42 positioned on either side of anchor 9. Anchor-receiving tip 52 also has a cylindrical slot 54 aligned with the longitudinal axis of tip 52. Cylindrical slot 54 should correspond in size and shape to cylindrical end 45 of anchor 9 in order to matingly receive the same. It is also preferable that the distance between guide tabs 53 be slightly smaller than the distance between the corresponding grooves 42 on anchor 9. In this fashion, guide tabs 53 as well as cylindrical slot 54 will apply compressive force against anchor 9 thereby more securely holding anchor 9 in place when loaded within anchor-receiving tip 52.

Since suture 10 will extend outwardly on either side of anchor 9, it is preferable to provide a means for ensuring that suture 10 is not abraded by the bone surrounding the bore during the insertion process. Thus, a pair of tapered grooves 55 are provided on either side of the anchor insertion tool, and extend from the end of anchor-receiving tip 52 along at least a portion of the length of elongate member 50. As best shown in FIG. 10 wherein anchor 9 has been loaded upon the insertion tool, grooves 55 ensure that the sutures will be protected by anchor-receiving tip 52 and a portion of elongate member 50 during the insertion process. Since any nicks in the suture may compromise the strength and permanency of the fixation, it is important to ensure that the suture is not damaged in any fashion.

Anchor-receiving tip 52 should also be of the proper length to ensure deep placement of anchor 9 completely within the bore. Thus, the length of the combination of anchor-receiving tip 52 and bone anchor 9 when loaded in the manner shown in FIG. 10 should be equivalent to the size of the bore created in the pubic bone. Since the diameter of elongate member 50 is significantly greater than that of anchor-receiving tip 52, distal end 56 of elongate member 50 will firmly abut the pubic bone once the anchor has been completely inserted into the bore. In this manner, the surgeon can be certain that the anchor has been seated to its complete and proper depth.

As was the case with the drill tamper tool of the present invention, elongate member 50 further comprises an intermediate section 57 and a guide portion 58. Intermediate portion 57 should have a diameter sufficiently less than that of the laparoscope in order to provide adequate vision for the surgeon, and intermediate portion 57 also has distal end 56 described above. Preferably, intermediate portion 57 has a length between about 2 and about 6 cm, most preferably about 5 cm. It should be kept in mind that, as shown in FIG. 10, suture 10 will extend along the length of intermediate portion 57 on either side thereof. This consideration must be kept in mind when sizing the diameter of intermediate portion 57 to ensure not only that it can be easily inserted through the laparoscope, but also to ensure adequate vision.

Guide portion 58 will necessarily be slightly smaller than the diameter of the guide portion for the drill tamper tool previously described, since, as shown in FIG. 10, suture 10 will extend along either side of guide portion 58. With this in mind, the total of the diameter of guide portion 58 and twice the diameter of suture 10 should be only slightly less than the inside diameter of the operative channel of the laparoscope. In this fashion, guide portion 28 provides a rigid support for the surgeon during the anchor insertion process. Preferably, guide portion 58 has a length between about 50 and 55 cm., most preferably about 52 cm. This provides an overall inserter length comparable to that of the drill tamper tool, thereby providing the same advantages with regard to the tamper tool length.

In order to effectively employ the procedure of the present invention laparoscopically, it is necessary that the two tails of suture 10 be controlled as much as possible. If the sutures are permitted to hang away from anchor 9 or the anchor insertion tool, the tails will generally become balled within the space of retzius, thereby making the suture tying procedure difficult, if not impossible. Although the sutures may be held against the anchor insertion tool by hand, Applicant has developed a more effective manner of accomplishing this. Thus, first and second shouldered depressions 59 and 60 are preferably provided about the circumference of guide portion 58. A small rubber band 61 (as shown in FIG. 10), or other suitable elastic band, may be held within each of the two shouldered depressions, with the two tails of suture 10 held beneath rubber band 61 on either side of guide portion 58 as shown. First shouldered depression 59 is preferably positioned approximately 10 cm from the ends of guide tabs 53. Second shouldered depression 60 is preferably positioned about 40 cm from guide tabs 53. Both shouldered depressions act, in conjunction with an elastic band contained therein, to hold suture 10 in place on the sides of the anchor insertion tool.

Figure 20:
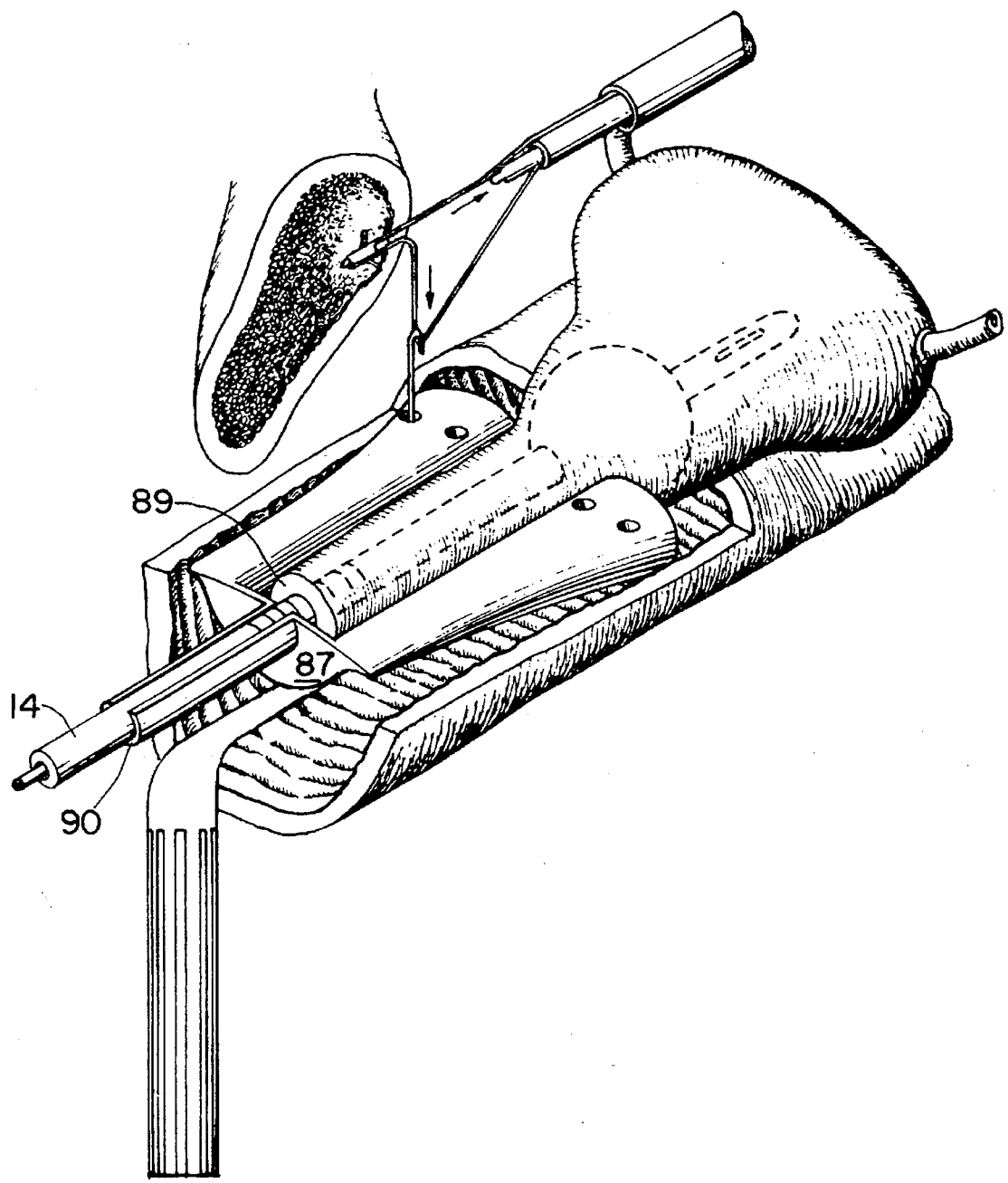
FIG. 20 is a perspective view of the surgical procedure of the present invention wherein portions of the patient's anatomy cut-away for clarity, and wherein the suture retriever of FIG. 11 is being employed.

In addition to holding the suture in place on the anchor insertion tool, the shouldered depression/elastic band combination further improves the laparoscopic procedure of the invention by not only assisting in seating the anchor, but also in the suture retrieval process. As shown in FIG. 20, the anchor insertion tool of the present invention, with a pre-loaded anchor and suture assembly attached thereto, is inserted through the laparoscope for placement of the anchor as previously described. Once the anchor has been seated within the bore, the anchor insertion tool is then pulled outwardly utilizing handle 51 contained thereon. The combination of shouldered depressions 59 and 60 and rubber-band 61 act to provide tension in suture 10 which in turn pulls outwardly on anchor 9 which is now contained in the bore. This outward force on anchor 9 will cause flexible barbs 41 to extend outwardly into the cancellous bone surrounding the bore, thereby further securing anchor 9 in position. In other words, this outward force on suture 10 by the drag created by the shoulder depression/elastic band combination will act to deploy the previously compressed barbs 41 on anchor 9, thereby rigidly securing anchor 9 within the bore.

In order to facilitate the surgical procedure of the present invention, the drill tamper tool and the anchor-insertion tool described above may be provided in the form of a reusable surgical kit.

D. Fixation of Periurethral Tissue at the UVJ Via Suturing

Once the anchor and suture assembly have been secured within the bore created in the pubic bone, it is next necessary to utilize the two tails of the suture to elevate the periurethral tissue on the corresponding side of the urethra at the UVJ. Applicant has found that the most effective means for accomplishing this is to pull each tail of the suture through the periurethral tissue into the vagina. In this fashion, the two tails may then be easily tied to one another within the vagina to provide the necessary support, and eliminating any need for laparoscopic suture tying. Obviously, however, a means for retrieving the suture tails must be provided.

The method of suture retrieval doing is best shown in FIG. 20, which is a perspective view of the procedure with portions of the patient's anatomy cut-away for purposes of clarity. As shown in FIG. 20, as the anchor insertion tool of the present invention is partially withdrawn from the patient through the laparoscope, first shouldered depression 59 in combination with rubberband 61 will cause both suture tails to be tensioned between the anchor and the anchor insertion tool as shown. Were this not the case, the suture tails would merely fall into the space of Retzius similar to a ball of yarn, and thereby be difficult (if not impossible) to retrieve. While the suture tails could be tensioned between the anchor and the anchor insertion tool by pulling outwardly on the sutures, this would unnecessarily require an additional pair of hands. Thus, the shouldered depression/rubber band combination is also effective in this regard.

Once the anchor insertion tool has been partially removed in order to tension the suture tails in the manner shown in FIG. 20, a suture retrieving tool may be inserted into the vagina and then pressed upwardly on one side of the urethra into the space of Retzius in order to retrieve one of the suture tails in the manner shown. Thus, the suture retrieving tool must have a sharp point capable of passing completely through the full thickness of the periurethral fascia and vaginal mucosa adjacent the urethra. The suture retrieval tool must also have a means for grasping the suture tail and pulling the tail back through the full thickness of the periurethral and vaginal mucosa by means of the same entry hole created by the sharp point. Each tail is pulled into the vagina in this fashion at the proper location. Preferably, one tail is pulled into the vagina approximately 1 cm from the urethra at the UVJ, and the other tail is pulled into the vagina approximately 2 cm lateral from the urethra. In other words, each tail penetrates the periurethral tissue along an imaginary line extending substantially perpendicularly away from the urethra. Each tail may then be pulled out of the vagina for purposes of tying.

The suture tails are tied to one another using a series of standard surgeon's knots, and each knot is slid by hand to the point in the vagina at which the suture tails were previously retrieved. The tails are tied to one another in a sufficiently tight fashion so that suture 10 creates an upward force on the periurethral tissue adjacent the urethra in order to elevate the urethra at the UVJ and restore the urethra to its proper angle. The position of the urethra can be readily observed by the surgeon as this procedure is performed, thereby ensuring that the urethra is restored to the desired angle. The entire procedure (anchor insertion, suture retrieval, etc.) is then repeated for the anchor placed on the opposite side of the pubic symphysis, and the suture tails of that anchor are pulled into the vagina through the periurethral tissue on the opposite side of the urethra as the first suture tails. Tying is then performed in the same fashion, thereby elevating the other side of the urethra to thereby completely restore the urethral angle at the UVJ.

The result of this process is best shown in FIG. 2, wherein it is shown that suture 10, and the corresponding suture on the opposite side of the urethra have restored the urethra to its proper angle. It should be noted that at no time do the sutures pull upward directly beneath the urethra, since doing so would create the risk that the suture would cause urethral blockage. After tying, the remaining tails of suture 10 are cut at the knot. The portion of suture 10 remaining in the vagina will epithelize within three to four days, and the patient will no longer sense that the sutures are in place. The result is a permanent fixation of the periurethral tissue on both sides of the urethra, thereby restoring the urethra to its correct angle and eliminating the SUI. After completion of the tying process, the surgical area within the patient is flushed with a dilute lidocaine solution, the laparoscope and trocars removed, a stronger lidocaine solution is applied to the incision sites, and the incisions are closed in the usual fashion. The Foley catheter may then be removed, and the patient permitted to recover in the usual fashion. Normal everyday activities may be resumed within 2–3 days.

E. Suture Retriever

In order to pull the tails of suture 10 through the entire thickness of the periurethral fascia and vagina mucosa, various tools can be employed. For example, a U.S. Surgical Auto-Stitch tool may be effectively employed for this purpose. It is critical, however, that the tool employed being capable of readily be inserted through the periurethral tissue from the vagina into the space of Retzius, while also being capable of grasping the suture tails. It is also critical that the surfaces contacting suture 10 be perfectly smooth in order to eliminate the risk of nicks or cuts in suture 10 which would obviously compromise the effectiveness of the procedure. Applicant has developed a novel suture retriever for accomplishing this purpose which provides a convenient and simple means of retrieving the suture tails.

The suture retrieval tool of the present invention is depicted in FIG. 11, and comprises metal retrieving end 65, midshaft 66, and handle 67. Midshaft 66 and handle 67 may be singularly molded from polycarbonate or a similar FDA-approved material in the typical fashion. As shown in FIG. 12, handle 67 is also preferably knurled in order to facilitate grasping and manipulation of the retriever. Metal retrieving end 65 is preferably made of stainless steel and can be securely molded into distal end 68 of midshaft 66.

Metal retrieving end 65 comprises a rigid, rod-like shaft 69, and a sharp tip 70 capable of penetrating the periurethral tissue. The diameter of distal end 68 is preferably significantly greater than that of shaft 69, and will act as a stop in order to limit the penetration of the suture retrieval tool into the space of Retzius. Thus, the length of shaft 69 and tip 70 may be selected so as to ensure that when the suture retrieval tool is inserted into the space of Retzius through the vagina that sharp tip 70 will generally be incapable of striking any surrounding soft tissue.

Retrieving end 65 further comprises a return leg 71 which extends away from sharp tip 70 in the same direction of shaft 69. Shaft 69, return leg 71 and the underside of sharp tip 70 thus create an inverted U-shaped region capable of ensnaring suture 10 for retrieval purposes. The distance between return leg 71 and shaft 69 in the region of the inverted U-shape is preferably approximately the same diameter as suture 10. In this fashion, and as shown in FIG. 20, after sharp tip 70 has penetrated the periurethral tissue adjacent the vagina in order to enter the space of Retzius, the inverted U-shape may be pulled downwardly over a suture tail, thereby snaring the suture. Metal retrieving end 65 may then be pulled back through the periurethral tissue, and the tail of suture 10 will remain snared between return leg 71 and shaft 69 directly beneath sharp tip 70. Although the suture tail will slide within the U-shaped region, it will nevertheless be pulled into the vagina.

One critical feature of the suture retriever of FIG. 12 is that the inner surfaces of metal retrieving end 65 which contact suture 10 must be rounded and smooth in order to permit suture 10 to freely slide within the inverted U-shaped portion as the retriever is withdrawn. This prevents nicking or fraying of the suture while still permitting the suture tail to be withdrawn. Thus, the only sharp portion of metal retrieving end 65 is sharp tip 70.

While it is possible that handle 67, midshaft 66, and metal retrieving end 65 may all be positioned along the same longitudinal axis thereby forming a rigid, elongate structure, Applicant has found that the process of the present invention can be simplified if the elements of the retriever have the angular relationship indicated in FIG. 11. This is particularly true when the template of the present invention (to be described further herein) is employed. Thus, metal retrieving end 65 preferably is positioned at an angle of between about 50 degrees and about 80 degrees, most preferably about 60 degrees, to midshaft 66 (this angle is indicated as A in FIG. 11). Likewise, handle 67 is preferably positioned at an angle of between about 50 degrees and about 80 degrees, most preferably about 60 degrees, to handle 67 (this angle is indicated as B in FIG. 11). Thus, the longitudinal axis of shaft 69 of metal retrieving end 65 will be parallel to the longitudinal axis of handle 67. In this fashion, when the retriever of the present invention is employed midshaft 66 will generally be positioned parallel to the longitudinal axis of the vagina. Metal retrieving end 65 will then extend upwardly through the periurethral tissue into the space of Retzius as desired. As best shown in FIG. 20, handle 67 will thereby extend downwardly outside of the vagina, and thus sharp tip 70 may be readily forced through the periurethral tissue as desired merely by pushing upwardly on handle 67.

As shown in FIG. 11, the transitions between handle 67 and midshaft 66 as well as between midshaft 66, and retrieving end 65 should be gently curved in order to ease placement. It should be noted that angles A and B can vary significantly, however it is preferred that they be as close to one another as possible so that the parallel relationship of handle 67 and retrieving end 65 is maintained. In addition, the present configuration ensures that the retrieving end 65 will enter the space of Retzius at an angle of approximately 90 degrees to the tensioned suture tails (i.e., the suture tails tensioned between the anchor and the anchor insertion tool). This perpendicular relationship allows for effective snaring of the suture, as well as improved vision of the retrieval through the laparoscope.

Preferably, midshaft 66 is between about 2 and about 6 cm. in length, most preferably about 4 cm. The cross-sectional area of midshaft 66 should merely be a size chosen to provide the necessary rigidity while also not blocking vision within the vagina during the procedure. Likewise, handle 67 is preferably about 4 cm long, however the length is not as critical since handle 67 remains completely outside of the body. The diameter of handle 67 should be chosen so as to provide a comfortable and secure means of grasping the suture retrieval tool. Preferably, handle 67 is about 3 cm in diameter.

F. Surgical Template

While the placement of the sutures at the UVJ may be accomplished by merely feeling for the correct location within the vagina by hand, particularly in relation to the ball of the Foley catheter, Applicant has developed a novel template which greatly simplifies proper placement of the sutures. This device not only prevents bladder injury, urethral injury, or vascular accidents, the template also ensures a proper distance between the two suture tails to ensure that there is adequate periurethral tissue between the tails to provide the necessary support. Obviously if the suture tails are placed too close to one another, there is a risk that the suture will tear through the periurethral tissue and eliminate the fixation. Thus, a template is provided wherein the template has at least two apertures which may be properly positioned on either side of the urethra. The suture retriever may then be inserted through these apertures and thereafter through the periurethral tissue in order to snare the suture tails in the manner described previously.

The presently preferred template is depicted in FIGS. 13–17. The template comprises a trough 80 of arcuate cross-section, wherein trough 80 is sized so as to cradle the patient's urethra when properly positioned. First and second wing members 81 and 82 extend away from opposite sides of trough 80, preferably perpendicularly to the longitudinally axis of trough 80 in the manner shown. Most preferably wing members 81 and 82 extend perpendicularly away from opposite sides of trough 80 at the upper most edges 83 and 84 of trough 80. First and second suture guide apertures 85 and 86 are positioned in each of the wing members 81 and 82 as shown. The guide apertures are positioned so that when the urethra of the patient is properly positioned within trough 80, guide apertures 85 and 86 on each wing will indicate the proper location for the sutures. First suture guide aperture 85 is positioned so that the first tail of suture 10 will penetrate the periurethral tissue approximately 1 cm from the urethra adjacent the UVJ. Second guide aperture 86 is preferably positioned about 1 cm further away from the urethra along a line perpendicular to the longitudinal axis of trough 80. In other words, the distance between first suture guide aperture 85 and second suture guide aperture 86 is preferably about 1 cm. In this manner, the surgeon can be confident that sufficient periurethral tissue will be present between the two suture tails.

Figure 13:
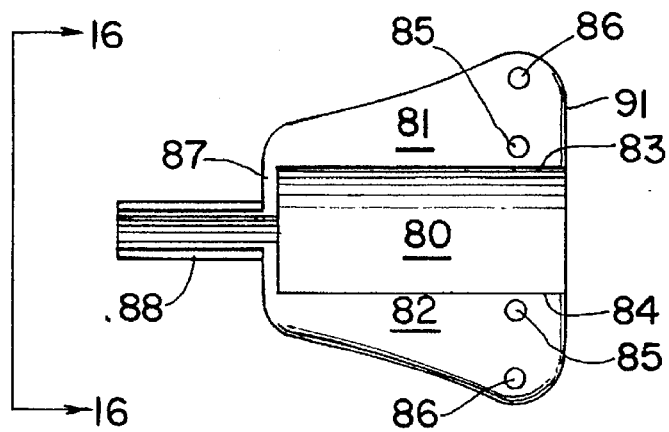
FIG. 13 is a top plan view of a suture template of the present invention.
Figure 14:
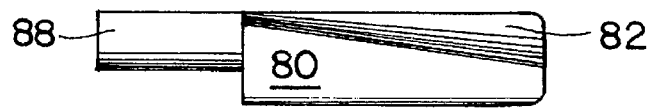
FIG. 14 is a side plan view of the template of FIG. 13.
Figure 15:
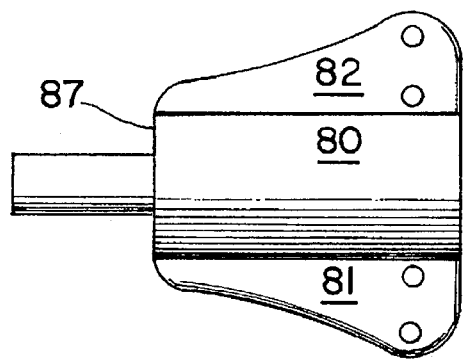
FIG. 15 is a bottom plan view of the template of FIG. 13.
Figure 16:
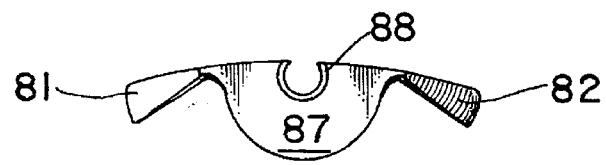
FIG. 16 is an end plan view of the template of FIG. 13, taken along line 16—16 thereof.

It is certainly possible that the template of the present invention may merely be held in place by hand, and in fact the downwardly sloping nature of the underside wing members 81 and 82 are suitable for placement of the surgeon's fingers thereunder. Additional alignment means are preferably provided, however at a minimum, end wall 87 is provided at the end of trough 80 furthest away from the suture guide apertures. Thus, as long as the template is properly sized for the length of the patient's urethra, the surgeon may hold the template in place with end wall 87 abutting the outermost end 89 of urethra 4 in order to ensure proper alignment. For example, if the length of the patient's urethra is determined to be three cm, the distance between end wall 87 and first and second guide apertures 85 and 86 should be between about 2.5 and about 3.2 cm, most preferably about 2.8 cm. The guide apertures should also be between about 0.25 and about 0.5 cm from distal end 91 of the wing members (FIG. 13). As long as the template is positioned with end wall 87 abutting the outermost portion of the urethra, the surgeon will be assured that the sutures will be properly placed without risk of puncturing the bladder, or urethra.

While the surgeon may employ two fingers beneath wing members 81 and 82 to hold the template in the proper position, Applicant has found that the provision of arcuate alignment member 88 secured to end wall 87 may be effectively employed for securing the template in place without the need for the surgeon to hold the template in any manner. Alignment member 88 is preferably positioned parallel to trough 80, with the center line of alignment member 88 aligned with the center line of trough 80. Alignment member 88 may either extend away from trough 80 as shown in FIG. 13, or alternatively may extend away from end wall 87 directly along the interior of trough 80 as shown in FIG. 18.

When the embodiment of FIGS. 13–16 is employed, alignment member 88 is preferably sized so that when the template is manufactured from a resilient material, alignment member 88 may be rigidly snapped about Foley catheter 14 as shown in FIG. 20. Thus, the shaft of Foley catheter will be securely held within alignment member 88, and the surgeon need only pull outwardly on the Foley catheter while sliding the template into the vagina towards the urethra until end wall 87 abuts end 89 of urethra 2. The ball of the Foley catheter will thus be positioned at the UVJ, and the template will likewise be positioned at the appropriate location assuming that a template of the proper size has been selected based upon the length of the urethra.

As an alternative to providing various sizes for the template of the present invention, a single, larger-sized template may be employed provided that alignment member 88 is snapped about the shaft of Foley catheter 14 in the proper location. Thus, instead of abutting end wall 87 against end 89 of urethra 2, end wall 87 is instead aligned with the appropriate graduation along the shaft of Foley catheter 14 based upon the previously-measured length of the urethra. Likewise, end 90 of alignment member 88 could alternatively be aligned with the appropriate graduation along the shaft of Foley catheter 14 in order to provide the proper placement of the template based upon the length of the patient's urethra.

Figure 18:
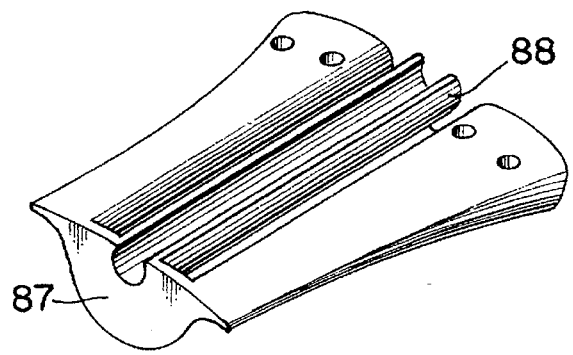
FIG. 18 is a perspective view of an alternative embodiment of the suture template according to the present invention.

FIG. 18 depicts yet another alternative embodiment for the template of the present invention in which alignment member 88 extends along the interior of trough 80. In employing this embodiment, alignment member 88 is inserted into the urethra along with Foley catheter 13 until end wall 87 of the template abuts end 89 of urethra 2. As will be understood, therefor, an appropriately-sized template will ensure proper placement of the sutures.

Finally, the template of the present invention can be manufactured of any suitable material such as polycarbonate or other FDA-approved plastic. The template may be readily molded using known technology, and is preferably manufactured as a disposable, single-use item. The drill tamper tool and anchor insertion tools, on the other hand, should be made from medical-grade stainless steel. The handles, however, may be polycarbonate or other FDA-approved plastic.

Alternative, and Presently Preferred Anchor and Anchor-Insertion Tool

Figure 19:
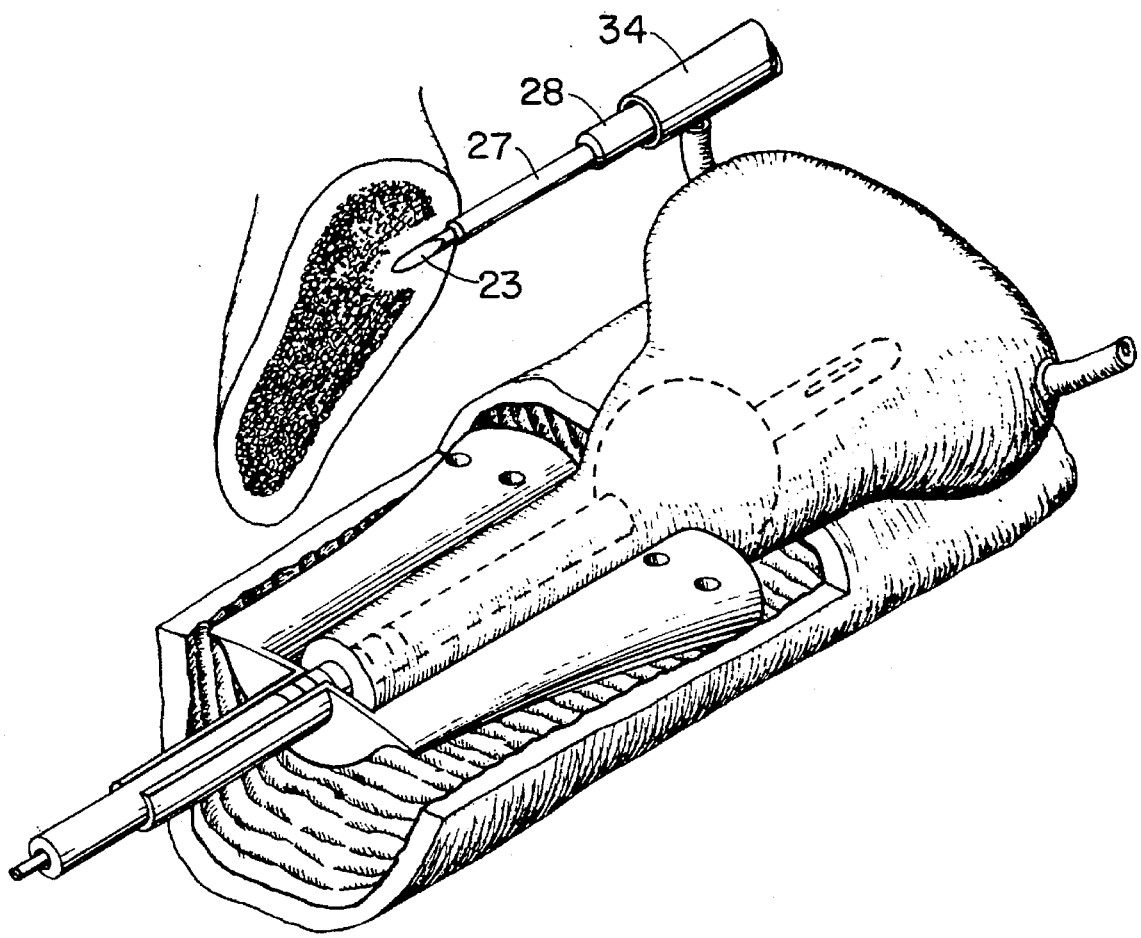
FIG. 19 is a perspective view of the insertion tool of FIG. 8 in use during a surgical procedure with portions of the patient's anatomy cut-away for clarity.
Figure 23:
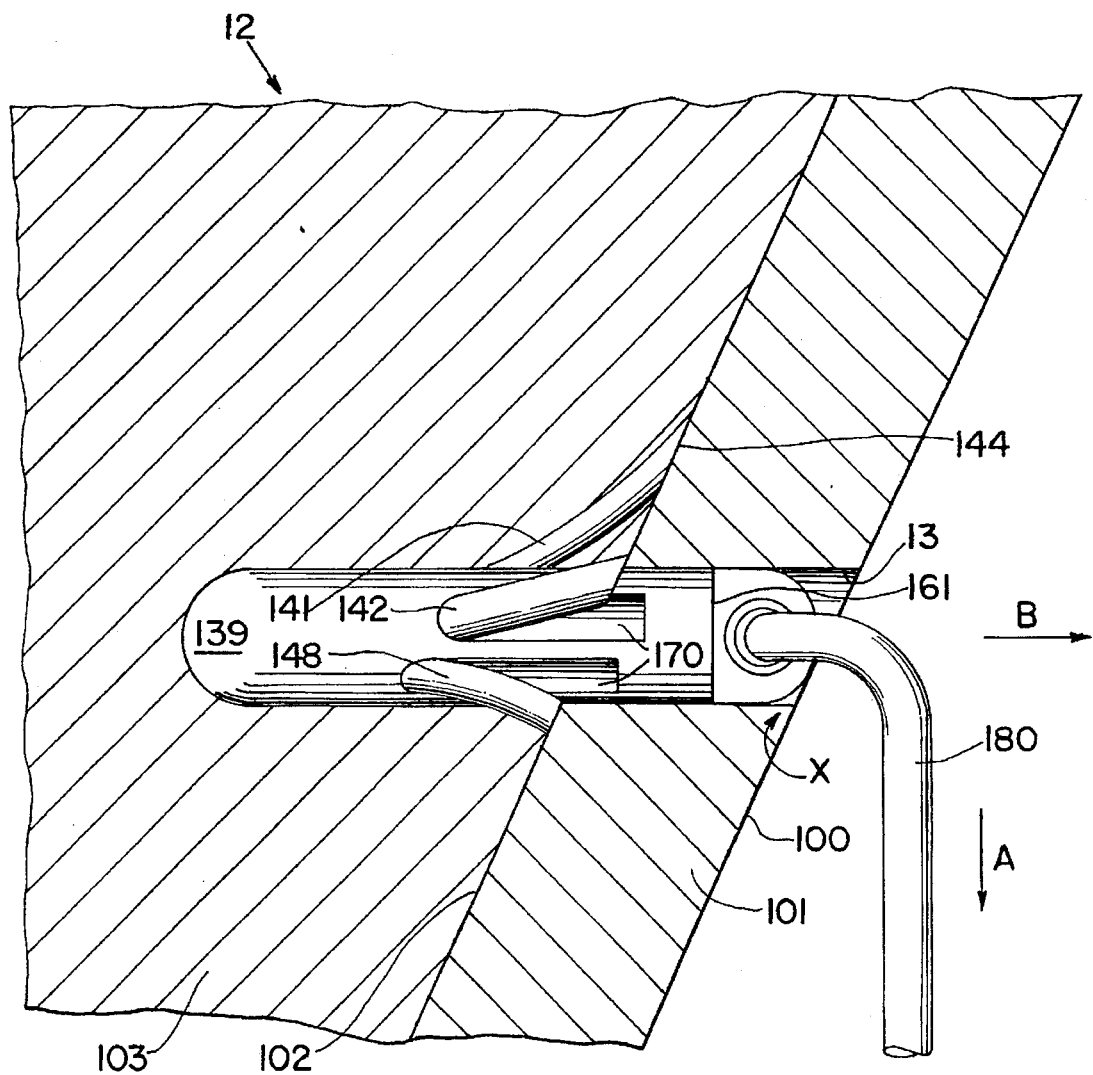
FIG. 23 is a side plan view of the anchor of the present invention in place in the pubic bone of a patient, wherein the pubic bone is shown in cross-section.

As mentioned previously, and as best shown in FIG. 19, pubic bone 12 falls away from the laparoscope at an angle of about 45° to 60°. Thus, it is impossible to create a bore in the pubic bone which extends perpendicularly from the surface of the bone. Thus, the bore produced in pubic bone 12 extends inwardly at an angle of between about 20° and about 60°. In other words, as shown in FIG. 23 which is a cross-sectional view of pubic bone 12, when bore 13 is viewed in cross-section as shown, the angle between surface 100 of the pubic bone and bore 13 at X will be between about 20° and about 60°, preferably about 45°. During the laparoscopic surgical procedure of the present invention, the surgeon may readily modify angle X in order to provide an angle which corresponds to that of the anchor to be described (preferably about 45°). This may be accomplished by inflating or deflating the abdominal cavity as needed in order to change the angle of the laparoscopic channel in relation to the pubic bone. Since interior surface 102 of cortical bone 101 is parallel to outer surface 100 of pubic bone 12, this same angular relationship will exist within the interior of the bore. When an anchor such as that disclosed in FIGS. 3 and 4 is employed, one will immediately recognize that this angular relationship of surface 102 and bore 13 will only permit the lower barb of the anchor to contact surface 102. Since cancellous (or tribecular) bone 103 offers very little support for the anchor, only the contact between the lower most barb of the anchor of FIGS. 3 and 4 and surface 102 provides the principle support which prevents the anchor from being pulled out of the bore.

When anchors of the type shown in FIGS. 3 and 4 are tested for pull-out strength, they are typically pulled only in the direction of arrow B. After the urethropexy procedure of the present invention is accomplished, however, any force on the anchor is most often in the direction of arrow A. As will be readily understood, due to that fact that only the lower barb will be in contact with surface 102, it is possible for the anchor to be pulled out of the bore due to forces acting in the direction of arrow A. This results from the fact that the end of the anchor to which the suture is secured is able to pivot downwardly in the direction of Arrow A since cancellous bone 103 offers little support.

Figure 24:
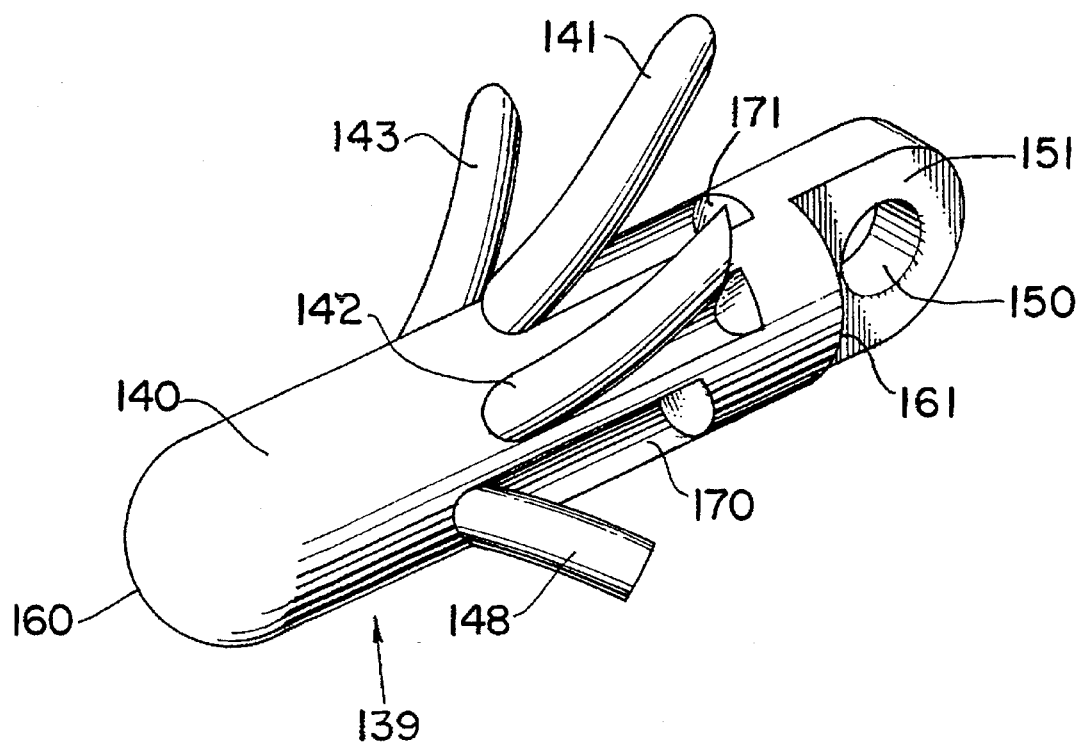
FIG. 24 is a perspective view of the anchor of FIG. 23.
Figure 25:
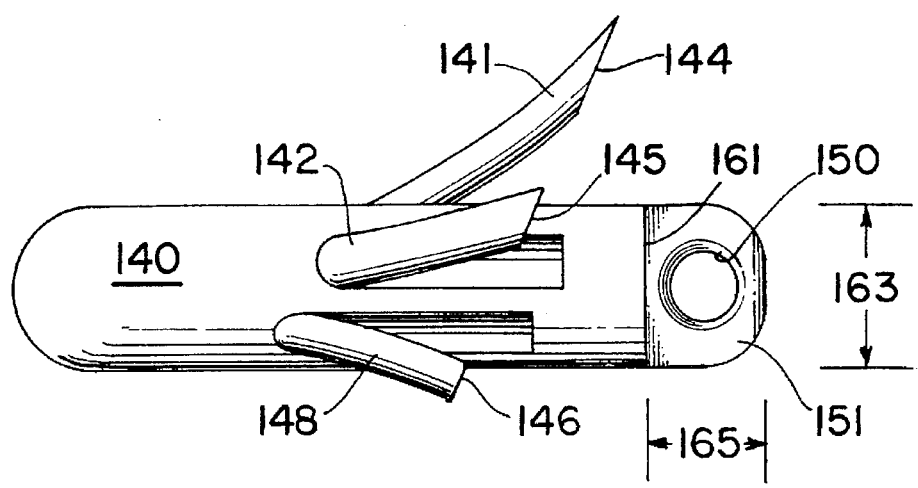
FIG. 25 is a side plan view of the anchor of FIG. 23.

In order to overcome the problems of the prior art anchor designs noted above, the present applicant has developed a new anchor design shown in FIGS. 23–30. The shortcomings of the prior art are overcome by modifying the orientation of the wing members or barbs to ensure that the external ends of the wing members (i.e., the portions which contact inner surface 102 of the cortical bone) have an angular relationship corresponding to the angular relationship between bore 13 and surface 102 (to be further described in detail below). Thus, as best shown in FIGS. 24 and 25, anchor 139 comprises cylindrical body 140, at least three wing members (barbs 141, 142 and 143), and aperture 150 positioned in tab member 151. Body 140 is similar to that of the prior art designs, however distal end 160 may be rounded since it is relatively easy to urge distal end 160 into cancellous bone as needed. The conical shape of the prior art design, however, will certainly work. Proximal end 161 is preferably perpendicular to longitudinal axis 162 of body 140 to thereby provide a flat proximal end surface which may cooperate with the new anchor-insertion tool to be described herein. Aperture 150 serves the same purpose described previously (i.e., a means for attaching a suture to the anchor), and once again the surfaces and edges of aperture 150 should be as smooth as possible to prevent fraying of the suture. In fact, aperture 150 may even be highly polished or even coated to reduce friction.

Figure 26:
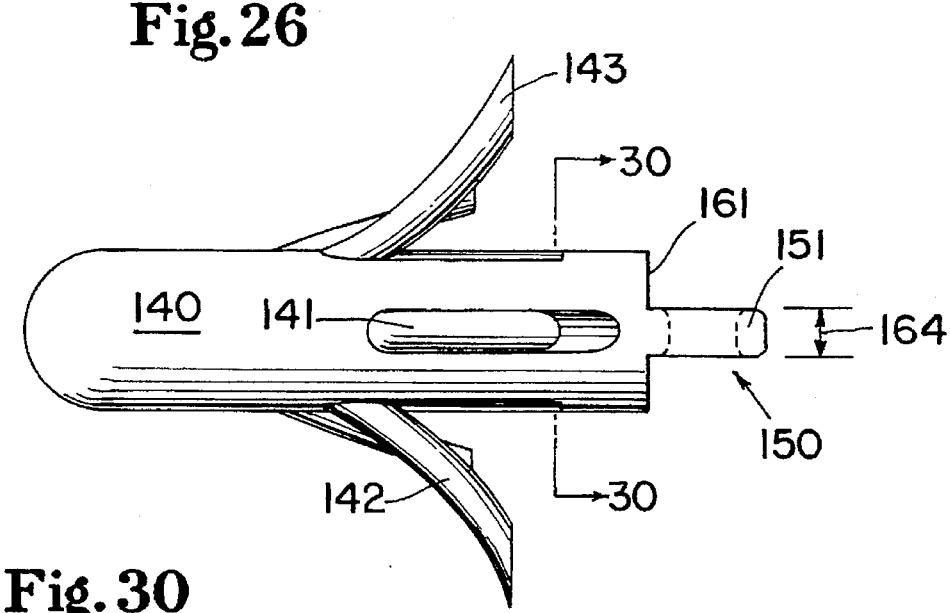
FIG. 26 is a top plan view of the anchor of FIG. 23.

Tab member 151, as shown in FIGS. 24–26, preferably has a height 163 corresponding approximately to the diameter of body 140 and a width 164 less than the diameter of body 140. The length 165 of tab member 151 should be sufficient for aperture 150 to permit a size 0 suture to be passed therethrough. It is also preferred that the length of tab member 151 extend perpendicularly away from proximal end 161 to facilitate cooperation and mating with the anchor-insertion tool to be described.

As mentioned above, the most significant feature of the anchor shown in FIGS. 23–30 is the arrangement of the wing member or barbs. As is the case with the prior art anchor design, the barbs may be elastically flexed (i.e., have memory) from the normal deployed position (as shown in the figures), to a compressed position. In the deployed position, the barbs preferably curvilinearly extend radially and axially away from body 140, as shown. In the compressed position, the barbs are substantially straightened to permit insertion of the anchor into a bore created in bone in the manner of the prior art (see, for example, U.S. Pat. Nos. 5,207,679 and 5,217,486 both of which are herein incorporated by way of reference). To facilitate compression and insertion, a plurality of channels 170 are provided along the length of body 140. One of channels 170 is positioned beneath each of the wing members, and is aligned therewith. Each of the channels is further sized so as to accept at least a portion of, and preferably the entirety of the corresponding wing member aligned therewith. In this manner, when a wing member is compressed during the anchor insertion process, the compressed and straightened wing member will be positioned entirely within channel 170 positioned adjacent the wing member.

With the wing members in this compressed state, the diameter of the anchor will be equivalent to that of body 140, thereby permitting the anchor to be inserted into a bore having a diameter only slightly greater than body 140. As the wing members extend into the bore beyond interior surface 102 of the cortical bone, the wing members will return to their deployed position, since the cancellous bone is not sufficiently hard to resist the spring-back of the wing members due to their inherent elasticity (or memory). As shown in FIG. 23, since the diameter of bore 13 is only slightly greater than body 140, the external ends of the wing members will abut against interior surface 102 thereby preventing removal of the anchor from the bore. For example, external end 144 of barb 141 is shown in FIG. 23 as resting against interior surface 102.

Figure 30:
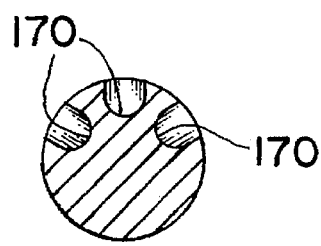
FIG. 30 is a cross-sectional view of the anchor of the present invention taken along the line 30—30 of FIG. 26.

The cross-sectional profile of channels 170 is shown in FIG. 30, which is a cross-sectional view of the anchor of FIG. 26. As shown in this view, channels 170 are preferably sufficiently deep to permit an entire wing member to be compressed into the channel. In addition, as shown in FIG. 24, the length of each channel 170 is only sufficiently long to contain the entire corresponding wing member when the latter is compressed. Thus, channels 170 may be of different lengths depending upon the various lengths of the corresponding wing members. End 171 of channel 170 (see FIG. 24) may also be angled in relation to the longitudinal axis 162 as shown in order to correspond with the external ends of the wing members, should these external ends be angled in the manner to be described.

Figure 25A:
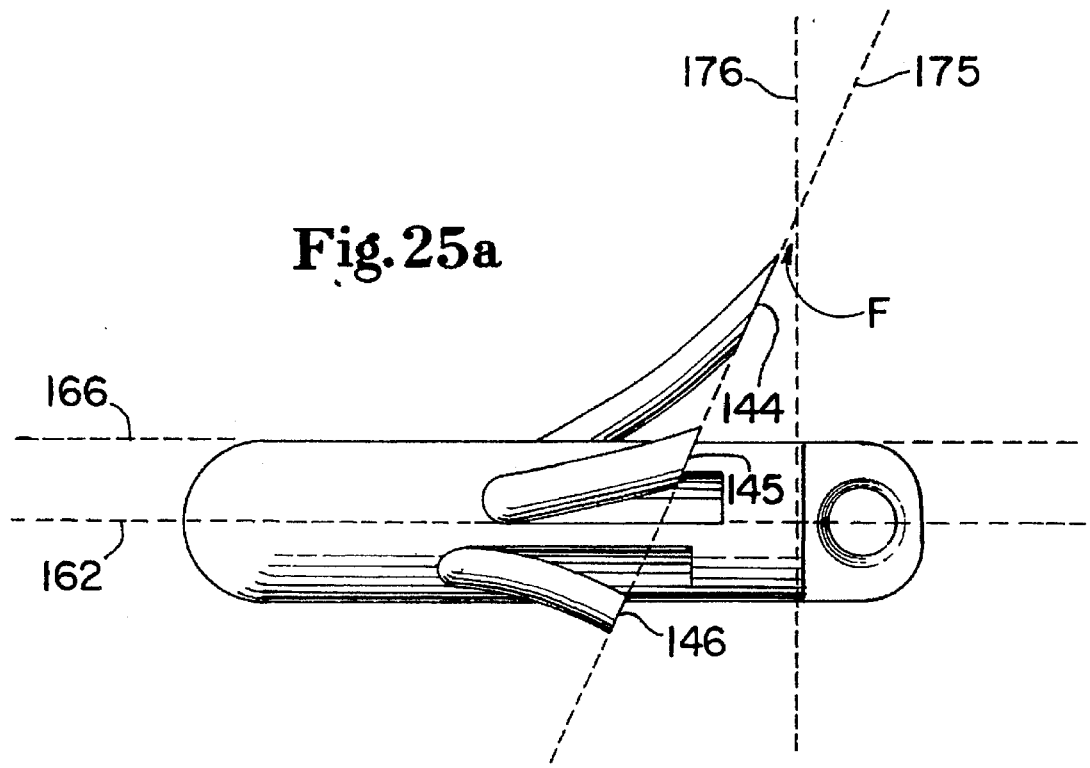
FIG. 25a is another side plan view of the anchor of FIG. 23.

In order to ensure that at least a portion of the external ends of each wing member contacts interior surface 102 of the cortical bone adjacent bore 13 when bore 13 is positioned non-perpendicularly to outer surface 100 of the pubic bone, at least a portion of the external end of each wing member is aligned along first imaginary plane 175 extending through body 140 (see FIG. 25a). In the prior art anchor designs this imaginary plane is perpendicular to longitudinal axis 162, thereby evenly aligning all of the external ends of the wing members. In the anchor of the present invention, however, first imaginary plane 175 extends through said body at an angle to transverse cross-section 176 through body 140, wherein cross-section 176 is perpendicular to longitudinal axis 162. As will be understood, angle F of FIG. 25a is preferably substantially equivalent to angle X of FIG. 23, thereby ensuring that at least a portion of the external end of each barb will contact interior surface 102 of the cortical bone adjacent bore 13. Thus, angle F is preferably between about 20° and about 60°, most preferably about 45°. The external ends of the wing members are more preferably tapered as shown so that the entirety of each external end will lie along first imaginary plane 175. Thus, external ends 144, 145 and 146 of corresponding barbs 141, 142, and 148 are aligned along plane 175, thereby adding further support when the anchor is secured within bore 13.

As will be more fully understood later, it is helpful at this point to also define the top of the anchor by a top-line 166 which extends along the surface of body 140 parallel to longitudinal axis 162. First imaginary plane 175 intersects top-line 166 at the point of intersection between the surface of body 140 and imaginary plane 175 which is nearest to proximal end 161. In other words, therefore, the barb extending from body 140 at point nearest to top-line 166 will also have an external end which is closest to proximal end 161. The further from top-line 166 that a barb extends from body 140, the further its external end will be from proximal end 161. The upper portion of body 40 is defined as that half of body 40 nearest to top-line 166, and the lower portion is therefore the remainder.

To provide the alignment described above, the wing members may extend from the anchor body in a number of fashions. Most preferably, however, each barb should be of a similar length in order to provide similar flexing characteristics for each barb thereby ensuring that the anchor will be urged straight into the bore. Thus, each wing member preferably extends from body 140 along a second imaginary plane extending through body 140 at an angle to cross-section 176. As will be understood, the angle between this second imaginary plane and cross-section 176 should be approximately equivalent to angle F of FIG. 25a. Alternatively, the wing members may extend from the anchor body at points equidistant from proximal end 161 (i.e., along a plane extending perpendicular to longitudinal axis 162). In order to provide the proper alignment for the external ends of the barbs, however, the length of the barbs in this embodiment would necessarily not all be equivalent to one another.

Figure 27:
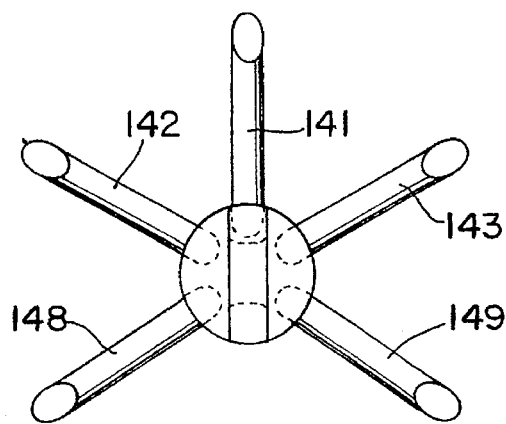
FIG. 27 is an end plan view of the anchor of FIG. 23, viewed from the proximal end towards the distal end.
Figure 28:
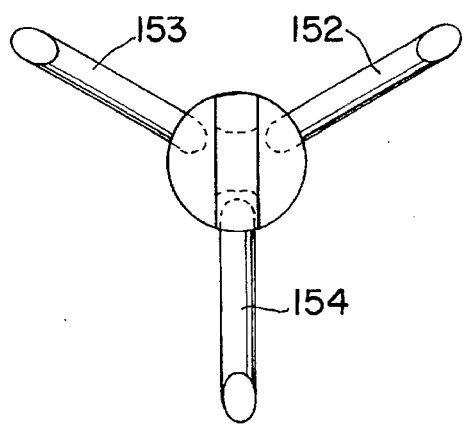
FIG. 28 is an end plan view of another embodiment of an anchor according to the present invention, viewed from the proximal end towards the distal end.
Figure 29:
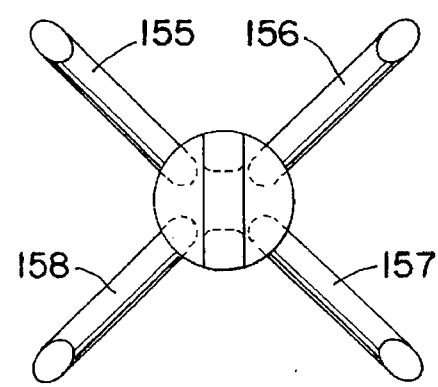
FIG. 29 is an end plan view of another embodiment of an anchor according to the present invention, viewed from the proximal end towards the distal end.

In order to provide proper support during use, various configurations and numbers of barbs may be employed. Three preferred arrangements are shown in FIGS. 27–29. In the embodiment of FIG. 27, which corresponds to that of FIGS. 23–26, five barbs are employed. Thus, barbs 141, 142, and 143 extend upwardly away from the upper portion of body 40, while barbs 148 and 149 extend downwardly away from the lower portion. When the anchor is viewed from the proximal end towards the distal end (FIGS. 27–29), it is seen that barb 141 is substantially aligned with the top-line of body 140. To simplify the description, this will be defined as the 12 o'clock position in terms of a standard clock face. Thus, barb 141 is at about 12 o'clock, barb 142 is between about 10 and 11 o'clock, barb 143 is between about 1 and 2 o'clock, barb 149 is between about 4 and 5 o'clock, and barb 148 is between about 7 and 8 o'clock. It should be pointed out that whenever an odd number of barbs are employed, it is preferable that a greater number of barbs extend from the upper portion of the body rather than the lower portion, since further support is needed in this area.

In the embodiment of FIG. 28, three barbs (152, 153 and 154) are employed, two of which extend from the upper portion of body 140. Preferably, barb 153 is between about 10 and 11 o'clock, barb 152 is between about 1 and 2 o'clock, and barb 154 is at about 6 o'clock. In the embodiment of FIG. 29, four barbs (155, 156, 157 and 158) are utilized, two extending upwardly away from the upper portion of body 140, and two extending downwardly away from the lower portion of body 140. Preferably, barb 155 is between about 10 and 11 o'clock, barb 156 is between about 1 and 2 o'clock, barb 157 is between about 4 and 5 o'clock, and barb 158 is between about 7 and 8 o'clock. It should be noted that any of a number of alternative configurations are possible, and the three shown are merely exemplary of the simplest and preferred embodiments.

The anchor of the present invention may be made of any of a number of materials, however titanium or titanium alloys are preferred. The anchor is also preferably singularly molded, however the wing members may be formed separately and attached to body 140 during the assembly process. For example, the wing members or barbs may be attached to body 140 in the manner described in U.S. Pat. Nos. 5,207,679 and 5,217,486 both of which are herein incorporated by way of reference. It is preferred, however, that the barbs comprise wire-like members, and may even be formed from titanium or nickel-titanium wires in a known fashion.

As also discussed previously, aperture 150 of anchor 139 is designed so that suture 180 may pass therethrough. In this fashion, two suture tails will extend from aperture 180, and may be used in the manner previously described to elevate the periurethral tissue at the UVJ, for example. It is important during such a procedure, however, that the suture be protected from nicks and other abrasions which would compromise suture strength. While the proximal end of the anchor shown in FIGS. 23–30 may be modified to that shown in FIGS. 3–4 so that the anchor-insertion tool of FIGS. 8–10 can be employed therewith, Applicant has developed yet another anchor-insertion tool which can be employed with the anchor design shown in FIGS. 23–30. This new anchor-insertion tool not only protects the suture, it also facilitates proper alignment of the anchor within the bore and also provides a means for tensioning the suture tails in the manner shown in FIG. 20.

An anchor-insertion tool according to the present invention is shown in FIGS. 31–35, and comprises a rigid elongate member 250 having:

anchor-receiving tip 252 hollow cylindrical intermediate portion 253 having distal end 260 adjacent anchor-receiving tip 252, intermediate portion 253 preferably having a diameter greater than the diameter of tip 252 handle 251 attached to intermediate portion 253 at the end opposite anchor-receiving tip 252 passageway 254 providing communication between the interior of intermediate portion 253 and the exterior of the tool, Since anchor-receiving tip 252 is also preferably hollow and its interior is in communication with the interior of intermediate portion 253, an anchor having a suture extending therefrom may be secured on tip 252, and the suture (preferably a pair of suture tails) will extend through tip 252, through at least intermediate portion 253, and through passageway 254. As shown in FIG. 31, passageway 254 is preferably provided in handle 251 and terminates on rear face 255 of handle 251. Since passageway 254 is in communication with the interior of intermediate portion 253, the suture tails may extend along the entire interior length of the tool, and exit at rear face 255 of handle 251. Thus, as shown in FIG. 32, suture tails 260 and 261 extend from anchor 139 held on tip 252, through the entire interior of the tool, and exit at rear face 255. Although the suture tails may exit from the interior of the tool at various other locations, rear face 255 provides a location convenient for the surgeon during laparoscopic urethropexy and similar procedures. In addition, the sutures are completely enclosed within the tool, and thus nicking or fraying cannot occur during the insertion process. It should be noted that the length of suture tails 260 and 261 has been shortened for purposes of clarity.

Anchor-receiving tip 252 should be structured so as to matingly engage the particular anchor being employed. In addition, as described previously, the diameter of tip 252 should be equivalent to that of the anchor body to facilitate anchor insertion. In the embodiment of FIGS. 31–32, tip 252 has a slot 256 extending across the diameter of the tip and at least partially along its length, slot 256 capable or matingly receiving tab member 151 of anchor 139. Since it is critical that anchor 139 be properly aligned within the bore in the pubic bone, slot 256 prevents rotation of the anchor during the anchor insertion process. Slot 256 is preferably sized equivalent to or slightly larger than tab member 151 of anchor 139, so that tab member 151 may be placed within slot 256. Tab member 151 may be wedged within slot 256 to hold the anchor on tip 252, or alternatively, end 258 of tip 252 may be secured to proximal end 161 of anchor 139 by means of a releasable adhesive. Any FDA-approved epoxy or other adhesive may be employed, as long as the bond between end 258 and proximal end 161 may be readily broken after the anchor has been seated within the bore merely by pulling the insertion tool away from the bore. In addition, since the suture tails are preferably tensioned between the anchor and handle 251 in a manner to be described, suture tails 260 and 261 will also act to keep tab member 151 held in place in slot 256.

As best shown in the cross-sectional views of FIGS. 33–34, the wall thickness of tip 252 should be such that suture 180 which extends through aperture 150 of the anchor tab member will not be compressed by the interior walls of tip 252 when the anchor is in place on tip 252. In other words, the interior diameter of anchor-receiving tip 252 is greater than the sum of the width of tab member 151 plus twice the diameter of suture 180. In this manner, suture 180 will be further spared from damage during the anchor insertion process.

As will be apparent, in order to properly seat anchor 139, anchor-receiving tip 252 should have a length sufficient to ensure that all of the barbs of the anchor are inserted past the cortical bone for proper barb deployment. Since it is preferred that proximal end 161 of anchor 139 be approximately aligned with interior surface 102 of the cortical bone surrounding the bore when the anchor is properly seated within a bore (i.e., external ends of all barbs resting against interior surface of cortical bone), it will be apparent that anchor-receiving tip 252 should have a length approximately equivalent to, or slightly greater than the thickness of the cortical bone (between about 5 mm and about 8 mm). End 260 of intermediate portion 253 not only acts to drive the anchor into the bore, but also acts as a stop since its diameter is preferably greater than the anchor body and the bore into which it is being inserted. Thus, the proper length for tip 252 will ensure not only that the anchor is driven sufficiently deep within the bore to fully deploy all of the barbs, but also to ensure that the anchor is not driven too far into the bore. In the latter situation, anchor stability may be compromised, and the suture may be damaged by the edges of the bore once the surgical procedure has been completed.

In order to facilitate manipulation of the anchor-insertion tool within the laparoscope, a plurality of ridges 259 are preferably provided about the circumference of intermediate portion 253. Ridges 259 are preferably positioned adjacent handle 151, most preferably between about 5 cm and about 10 cm from the handle. Since the diameter of intermediate portion 253 is preferably slightly smaller than the diameter of the laparoscope to be employed (preferably 7.8 mm and 8.0 mm respectively), ridges 259 will assist in controlling the insertion tool during the procedures of the present invention. Preferably, ridges 259 are sized so as to cooperate with the standard rubber grommet of a laparoscope.

Handle 252 may be secured to intermediate portion 253 by any of a number of means, however it is preferable that handle 252 be threadably secured to intermediate portion 253. Thus, corresponding male and female threads are provided on the handle and the intermediate portion. Once again handle 251 preferably has curved hand grip surfaces. In this embodiment, however, handle 251 preferably has dissimilar top and bottom portions 271 and 272, respectively. If anchor 139 is secured to tip 252 such that the top-line of the anchor is aligned with top portion 271 of handle 251, the surgeon can readily ensure that the anchor will be properly inserted into the bore. As long as top portion 271 extends directly upwardly during anchor insertion, proper placement will be guaranteed. In order to facilitate alignment, bottom portion 272 of handle 251 is preferably significantly heavier than top portion 271. This weight differential will further guarantee alignment, since gravity will cause the insertion tool to rotate within the laparoscopic channel to the correct position. It should be appreciated, however, that this alignment means (i.e., and oriented handle) requires that the engagement of handle 251 with intermediate portion 253 be precise. Of course other alignment means may be provided, such as guide lines, levelling bubbles, and the like.

As mentioned previously, providing tension in the suture tails extending from the anchor will not only help in maintaining the anchor on anchor-receiving tip 252, but will also assist during the suture retrieval step shown in FIG. 20 (i.e., when the insertion tool has been partially removed from the laparoscopic channel). Proper tensioning can be achieved by means of at least one notch into which the suture tail(s) may be wedged. Preferably, the notch(es) are positioned adjacent said passageway so that the suture tails may extend through the passageway directly into the notch(es). Thus notches 280 and 281 are preferably provided on rear face 255 of handle 251. In fact, passageway 254 preferably exits handle 251 in an elongated diamond-shaped exit 279, and thus notches 280 and 281 may comprise the opposing narrow corners of exit 279 as shown. When suture tails 260 and 261 leave passageway 254 through exit 279, each tail may be wedged within notches 280 and 281, respectively. In this manner, the tails will be tensioned between notches 280 and 281 and aperture 150 of the anchor. After the anchor has been inserted into the bore, and as the insertion tool is pulled partially out of the laparoscopically channel, suture tails 260 and 261 will slide within their respective notches, thus maintaining the desired tension in the suture tails as needed for the suture retrieval step. To further enhance the tensioning of the sutures, passageway 254 may taper from intermediate portion 253 towards exit 279, thereby providing an additional wedging of the suture tails within the final portions of passageway 254.

It should be noted that intermediate portion 253 preferably has a length of between about 52 cm and about 55 cm to facilitate its use through a laparoscope.

To facilitate a quick and proper anchor insertion process, anchor 139 and the anchor-insertion tool of the present invention may be provided to the surgeon in the loaded form of FIG. 32 (with suture attached and wedged for tensioning as shown). The anchor may even be releasably adhered to the anchor-receiving tip as shown. In this manner, the surgeon can merely open a sterile surgical kit containing preferably two pre-loaded insertion tools (i.e., anchor 139 engaged with anchor-receiving tip and suture tensioned between anchor and notches on handle 251). The pre-loaded insertion tools are sufficiently inexpensive to permit one-time use, or the manufacturer could provide a credit for the return of used anchor-insertion tools which can be sterilized and re-loaded. The surgical kit for performing laparoscopic urethropexy can also include a drill tamper tool, a suture retrieval tool, and/or one or more variously-sized templates (all of which have been described previously). In this fashion, the surgeon will have all of the tools necessary for a quick and simple urethropexy within a small sterile kit.

What I claim is:

1. An anchor securable within a bore created in bone, said anchor comprising:

(a) a body having a longitudinal axis, and proximal and distal ends;

(b) at least three wing members extending outwardly from, and secured to said body, each of said wing members capable of being elastically flexed from a normal deployed position to a compressed position, each of said wing members further having an external end positioned away from said body, at least a portion of said external ends of each of said wing members substantially aligned along a first imaginary plane extending through said body at an angle to a transverse cross-section through said body, said transverse cross-section perpendicular to said longitudinal axis; and (c) an aperture positioned adjacent said proximal end of said body.

2. The anchor of claim 1, wherein said body has upper and lower portions, wherein the top of said body is defined by a top-line extending along the surface of said body parallel to said longitudinal axis, wherein said first imaginary plane intersects said top-line at the point of intersection between the surface of said body and said first imaginary plane which is nearest to said proximal end, and wherein said angle between said first imaginary plane and said transverse cross-section is between about 20° and about 60°.

3. The anchor of claim 2, wherein said body is cylindrical.

4. The anchor of claim 3, wherein said proximal end of said body is substantially perpendicular to said longitudinal axis to thereby provide a flat proximal end.

5. The anchor of claim 3, further comprising a tab member extending from said proximal end of said body, wherein said aperture is positioned in said tab member.

6. The anchor of claim 2, wherein each of said wing members extends outwardly from said body along a second imaginary plane extending through said body at an angle to a transverse cross-section through said body, said transverse cross-section perpendicular to said longitudinal axis.

7. The anchor of claim 2, wherein each of said wing members extends outwardly from said body at points equidistant from said proximal end of said body, and wherein the length of each of said wing members is chosen so that at least a portion of the external end of each wing member will be substantially aligned along said first imaginary plane.

8. The anchor of claim 6, wherein said body further comprises a channel positioned directly beneath each of said wing members, each channel having a length at least as great as the portion of its corresponding wing member positioned externally of said body, such that said wing members will be positioned at least partially within said channels when the wing members are in said compressed position.

9. The anchor of claim 7, wherein said body further comprises a plurality of channels, one of said channels positioned directly beneath each of said wing members, each channel having a length at least as great as the portion of its corresponding wing member positioned externally of said body, such that said wing members will be positioned at least partially within said channels when the wing members are in said compressed position.

10. The anchor of claim 8, wherein each of said wing members comprises a cylindrical barb which, in its deployed state, curvilinearly extends radially and axially away from said body.

11. The anchor of claim 9, wherein each of said wing members comprises a cylindrical barb which, in its deployed state, curvilinearly extends radially and axially away from said body.

12. The anchor of claim 10, wherein said external end of each of said cylindrical barbs is tapered so as to substantially align the entirety of said external end along said first imaginary plane.

13. The anchor of claim 11, wherein said external end of each of said cylindrical barbs is tapered so as to substantially align the entirety of said external end along said first imaginary plane.

14. The anchor of claim 5, wherein said tab member has a width less than the diameter of said body.

15. The anchor of claim 3, wherein said anchor has three wing members, wherein one of said wing members extends downwardly away from the lower portion of said body, and wherein the two remaining wing members extend upwardly from the upper portion of said body.

16. The anchor of claim 15, wherein, when said anchor is viewed from the proximal end towards the distal end, said wing members extend from the circumference of said body at the following positions, wherein said top-line is defined as the 12 o'clock position: between about 10 and 11 o'clock; between about 1 and 2 o'clock; and about 6 o'clock.

17. The anchor of claim 3, wherein said anchor four wing members, wherein two of said wing members extends downwardly away from the lower portion of said body, and wherein the two remaining wing members extend upwardly from the upper portion of said body.

18. The anchor of claim 17, wherein, when said anchor is viewed from the proximal end towards the distal end, said wing members extend from the circumference of said body at the following positions, wherein said top-line is defined as the 12 o'clock position: between about 10 and 11 o'clock; between about 1 and 2 o'clock; between about 4 and 5 o'clock; and between about 7 and 8 o'clock.

19. The anchor of claim 3, wherein said anchor five wing members, wherein two of said wing members extends downwardly away from the lower portion of said body, and wherein the three remaining wing members extend upwardly from the upper portion of said body.

20. The anchor of claim 17, wherein, when said anchor is viewed from the proximal end towards the distal end, said wing members extend from the circumference of said body at the following positions, wherein said top-line is defined as the 12 o'clock position: about 12 o'clock; between about 10 and 11 o'clock; between about 1 and 2 o'clock; between about 4 and 5 o'clock; and between about 7 and 8 o'clock.

21. An anchor-insertion tool for laparoscopically inserting and securing an anchor within a bore created in bone, said anchor having at least one suture extending therefrom, said anchor-insertion tool comprising an elongate, rigid member having (a) an anchor-receiving tip, said tip capable of matingly engaging an anchor;

(b) a cylindrical hollow intermediate portion having one end adjacent said anchor-receiving tip, said intermediate portion having a diameter greater than the diameter of said anchor-receiving tip;

(c) a handle attached to said intermediate portion at the end opposite said anchor-receiving tip; and (d) a passageway providing communication between the interior of said intermediate portion and the exterior of said tool, such that a suture extending from an anchor portioned on said anchor-receiving tip may pass from said anchor-receiving tip, through at least a portion of said intermediate portion, and through said passageway;

further comprising at least one notch for holding a suture, wherein a suture may be wedged within said notch for tensioning the suture between an anchor positioned on said anchor-receiving tip and said notch, and further wherein said notch is sized such that the suture may slide within said notch as the anchor-receiving tip is moved away from an anchor to which the suture is attached.

22. The anchor-insertion tool of claim 21, further comprising a second notch for holding a suture, wherein both of said notches are positioned adjacent said passageway.

23. The anchor-insertion tool of claim 21, wherein said passageway extends through said handle.

24. The anchor-insertion tool of claim 21, wherein said anchor-receiving tip is hollow, wherein the interior of said tip is in communication with the interior of said intermediate portion, wherein said tip has a slot extending across the diameter of said tip and at least partially along the length of said tip, said slot positioned at an end of said tip opposite said intermediate portion.

25. The anchor-insertion tool of claim 23, wherein said handle is threadably secured to said intermediate portion.

26. The anchor-insertion tool of claim 23, wherein said intermediate portion has a plurality of ridges extending about its circumference, said ridges positioned adjacent said handle, wherein said ridges may interact with the operative channel of a laparoscope to provide enhanced control during use of said tool.

27. The anchor-insertion tool of claim 21, wherein said handle has a top portion and a bottom portion, said top and bottom portions aligned with said slot in said anchor-insertion tip, said bottom portion heavier than said top portion to facilitate proper insertion of an anchor when said tool is employed.

28. The anchor-insertion tool of claim 22, wherein said passageway extends through said handle, said passageway further has an elongated diamond-shaped exit such that said notches comprise opposing corners of said diamond-shaped exit.

29. A loaded anchor-insertion tool comprising, in combination, an anchor-insertion tool, an anchor and a suture, said anchor-insertion tool comprising an elongate, rigid member having:
   (a) an anchor-receiving tip, said tip capable of matingly engaging an anchor;
   (b) a cylindrical, hollow intermediate portion having one end adjacent said anchor-receiving tip, said intermediate portion having a diameter greater than the diameter of said anchor-receiving tip;
   (c) a handle attached to said intermediate portion at the end opposite said anchor-receiving tip;
   (d) a passageway providing communication between the interior of said intermediate portion and the exterior of said tool, such that a suture extending from an anchor portioned on said anchor-receiving tip may pass from said anchor-receiving tip, through at least a portion of said intermediate portion, and through said passageway; and
   (e) at least one notch for holding said suture;
said anchor matingly and releasably engaged with said anchor-receiving tip, said suture extending from said anchor through the interior of said intermediate portion and through said passageway, and said suture slidably wedged within said notch and tensioned between said anchor and said notch, and further wherein said notch is sized such that the suture may slide within said notch as the anchor-receiving tip is moved away from the anchor.

30. The loaded anchor-insertion tool of claim 29, wherein said anchor comprises:
   (a) a body having a longitudinal axis and proximal and distal ends;
   (b) a plurality of wing members extending outwardly from, and secured to said body, each of said wing members capable of being elastically flexed from a normal deployed position to a compressed position; and
   (c) an aperture positioned adjacent said proximal end of said body;
wherein said suture extends through said aperture.

31. The loaded anchor-insertion tool of claim 30, wherein said anchor receiving tip is hollow, wherein the interior of said tip is in communication with the interior of said intermediate portion, wherein said tip has a slot extending across the diameter of said tip and at least partially along the length of said tip, said slot portioned at an end of said tip opposite said intermediate portion, wherein said anchor further comprises a tab member extending from said proximal end of said body, said aperture positioned in tab member, said tab member having a width equivalent to or less than the width of said slot, and wherein said tab member is positioned within said slot thereby engaging said anchor with said anchor-receiving tip.

32. The loaded anchor-insertion tool of claim 31, wherein said anchor body and said anchor-receiving tip are both cylindrical and have approximately equivalent diameters, such that the end of said intermediate portion adjacent said tip may act as a stop when said loaded tool is employed to insert said anchor into a bore having a diameter less than the diameter of said intermediate portion.

33. The loaded anchor-insertion tool of claim 32, wherein the interior diameter of said anchor-receiving tip is greater than the sum of the width of said tab member plus twice the diameter of said suture, thereby permitting said tab member with said suture extending through said aperture to be positioned within said slot.

34. The loaded anchor-insertion tool of claim 31, wherein said anchor has at least three wing members extending outwardly from, and secured to said body, each of said wing members capable of being elastically flexed from a normal deployed position to a compressed position, each of said wing members further having an external end positioned away from said body, at least a portion of said external ends of said wing members substantially aligned along a first imaginary plane extending through said body at an angle of less than ninety degrees from a transverse cross-section through said body, said transverse cross-section perpendicular to said longitudinal axis.

35. The loaded anchor-insertion tool of claim 31, wherein said body has upper and lower portions, wherein the top of said body is defined by a top-line extending along the surface of said body parallel to said longitudinal axis, and wherein said first imaginary plane intersects said top-line at the point of intersection between the surface of said body and said first imaginary plane which is nearest to said proximal end; and wherein said handle has a top portion and a bottom portion, said top portion aligned with the top-line of said anchor body, said bottom portion of said handle extending downwardly away from said top portion, thereby facilitating proper alignment of said loaded tool during use.

36. The loaded anchor-insertion tool of claim 31, wherein said passageway extends through said handle, further comprising at least one notch positioned adjacent said passageway, said notch sized such that said suture is wedged within said notch, thereby tensioning said suture between said anchor and said notch.

37. The loaded anchor-insertion tool of claim 31, wherein said anchor is secured to said tip by means of a releasable adhesive.

38. A loaded anchor-insertion tool comprising, in combination, an anchor a suture, and an anchor-insertion tool for laparoscopically inserting and securing said anchor within a bore created in bone, said anchor comprising:
   (a) a body having a longitudinal axis, and proximal and distal ends;
   (b) at least three wing members extending outwardly from, and secured to said body, each of said wing members capable of being elastically flexed from a normal deployed position to a compressed position, each of said wing members further having an external end positioned away from said body, at least a portion of said external ends of each of said wing members substantially aligned along a first imaginary plane extending through said body at an angle to a transverse cross-section through said body, said transverse cross-section perpendicular to said longitudinal axis; and
   (c) an aperture positioned adjacent said proximal end of said body;
said anchor-insertion tool comprising an elongate, rigid member having:
   an anchor-receiving tip matingly and releasably engaged with said anchor;
   an intermediate portion having one end adjacent said anchor-receiving tip, said intermediate portion having a diameter greater than the diameter of said anchor-receiving tip; and
   a handle attached to said intermediate portion at the end opposite said anchor-receiving tip
wherein said suture extends from said aperture of said anchor.

39. The loaded anchor-insertion tool of claim 38, wherein said tip and said intermediate portion of said insertion tool are both hollow, said insertion tool further comprising a passageway providing communication between the interior of said intermediate portion and the exterior of said tool, wherein said suture extends from said aperture through said anchor-receiving tip, through at least a portion of said intermediate portion, and through said passageway.

40. A surgical kit for performing laparoscopic urethropexy, said kit comprising a pair of loaded anchor-insertion tools each of said anchor-insertion tools comprising an elongate, rigid member having:

(a) an anchor-receiving tip, said tip capable of matingly engaging an anchor;

(b) a cylindrical, hollow intermediate portion having one end adjacent said anchor-receiving tip, said intermediate portion having a diameter greater than the diameter of said anchor-receiving tip;

(c) a handle attached to said intermediate portion at the end opposite said anchor-receiving tip;

(d) a passageway providing communication between the interior of said intermediate portion and the exterior of said tool, such that a suture extending from an anchor portioned on said anchor-receiving tip may pass from said anchor-receiving tip, through at least a portion of said intermediate portion, and through said passageway; and (e) at least one notch for holding said suture;

said anchor matingly and releasably engaged with said anchor-receiving tip, said suture extending from said anchor through the interior of said intermediate portion and through said passageway, and said suture slidably wedged within said notch and tensioned between said anchor and said notch, and further wherein said notch is sized such that the suture may slide within said notch as the anchor-receiving tip is moved away from the anchor.

41. The surgical kit of claim 40, further comprising a drill tamper tool for laparoscopically creating a bore in the pubic bone of a patient.

42. The surgical kit of claim 41, further comprising a suture retrieval tool, said retrieval tool comprising:

(a) a retrieving end, said retrieving end comprising a rigid, rod-like shaft and a sharp tip capable of penetrating periurethral tissue, said shaft having a longitudinal axis; and (b) a handle, said handle having a longitudinal axis;

whereby said retrieving end may be inserted into a vagina, through the vaginal mucosa and periurethral tissue adjacent a urethra, and into the space of Retzius, such that said retrieving end may be employed to snare a suture positioned in the space of Retzius for retrieving said suture into the vagina.

43. The surgical kit of claim 42, further comprising at least one template for guiding said suture through the periurethral fascia and vaginal mucosa adjacent a patient's urethra during a urethropexy procedure after said anchor has been secured within the body of a patient above the patient's urethra, said template comprising:

(a) first and second wing members extending laterally from opposite sides of the template; and (b) at least one suture guide aperture positioned in each of said wing members at a predetermined location; said template configured to be alignable within the vagina of a patient such that one of said wing members will be positioned adjacent either side of said urethra with said at least one guide aperture in each wing member positioned such that a suture may be retrieved from within the patient's body through said at least one aperture.

* * * * *